US011401312B2

(12) United States Patent
Bechard et al.

(10) Patent No.: US 11,401,312 B2
(45) Date of Patent: Aug. 2, 2022

(54) CYTOKINE DERIVED TREATMENT WITH REDUCED VASCULAR LEAK SYNDROME

(71) Applicants: CYTUNE PHARMA, Nantes (FR); INSTITUT GUSTAVE ROUSSY, Villejuif (FR)

(72) Inventors: David Bechard, Saint-Etienne de Montluc (FR); Nathalie Chaput, Paris (FR); Melanie Desbois, Maison Alfort (FR)

(73) Assignees: Cytune Pharma, Nantes (FR); Institut Gustave Roussy (IGR), Villejuif (FR)

( * ) Notice: Subject to any disclaimer, the term of this patent is extended or adjusted under 35 U.S.C. 154(b) by 0 days.

(21) Appl. No.: 14/785,536

(22) PCT Filed: Apr. 22, 2014

(86) PCT No.: PCT/EP2014/001057
§ 371 (c)(1),
(2) Date: Oct. 19, 2015

(87) PCT Pub. No.: WO2014/170032
PCT Pub. Date: Oct. 23, 2014

(65) Prior Publication Data
US 2016/0068584 A1  Mar. 10, 2016

(30) Foreign Application Priority Data

Apr. 19, 2013 (EP) .................................. 13002066

(51) Int. Cl.
C07K 14/54 (2006.01)
A61K 38/20 (2006.01)
C07K 14/715 (2006.01)
G01N 33/50 (2006.01)
A61K 47/64 (2017.01)

(52) U.S. Cl.
CPC .......... C07K 14/5443 (2013.01); A61K 38/20 (2013.01); A61K 47/642 (2017.08); C07K 14/7155 (2013.01); G01N 33/5011 (2013.01); G01N 33/5047 (2013.01); C07K 2319/00 (2013.01); G01N 2800/52 (2013.01)

(58) Field of Classification Search
None
See application file for complete search history.

(56) References Cited

U.S. PATENT DOCUMENTS

| 4,671,958 A | 6/1987 | Rodwell et al. |
|---|---|---|
| 5,011,912 A | 4/1991 | Hopp et al. |
| 5,073,627 A | 12/1991 | Curtis et al. |
| 5,108,910 A | 4/1992 | Curtis et al. |
| 5,225,539 A | 7/1993 | Winter |
| 5,558,864 A | 9/1996 | Bendig et al. |
| 5,585,089 A | 12/1996 | Queen et al. |
| 5,595,721 A | 1/1997 | Kaminski et al. |
| 5,595,756 A * | 1/1997 | Bally ............... A61K 9/1272 264/4.1 |
| 5,645,835 A | 7/1997 | Fell, Jr. et al. |
| 5,677,171 A | 10/1997 | Hudziak et al. |
| 5,730,969 A | 3/1998 | Hora et al. |
| 5,736,137 A | 4/1998 | Anderson et al. |
| 5,821,337 A | 10/1998 | Carter et al. |
| 6,165,466 A | 12/2000 | Grabstein et al. |
| 6,235,883 B1 | 5/2001 | Jakobovits et al. |
| 6,344,192 B1 | 2/2002 | Grooten et al. |
| 6,787,132 B1 | 9/2004 | Gabizon et al. |
| 7,060,808 B1 | 6/2006 | Goldstein et al. |
| 7,112,436 B1 | 9/2006 | Rose-John |
| 7,198,781 B1 | 4/2007 | Revel et al. |
| 7,888,071 B2 | 2/2011 | Gillies et al. |
| 7,906,118 B2 | 3/2011 | Chang et al. |
| 8,124,084 B2 | 2/2012 | Lefrancois et al. |
| 8,287,865 B2 | 10/2012 | Hansen et al. |
| 8,951,524 B2 | 2/2015 | Birkle et al. |
| 2006/0025885 A1 | 2/2006 | Steffl et al. |
| 2006/0263857 A1 | 11/2006 | Lefrancois et al. |
| 2009/0105455 A1 | 4/2009 | Herrmann |
| 2009/0238791 A1 | 9/2009 | Jacques et al. |
| 2010/0150910 A1 | 6/2010 | Birkle et al. |

FOREIGN PATENT DOCUMENTS

| AU | 680909 | 8/1997 |
|---|---|---|
| EP | 0305967 A2 | 8/1988 |
| EP | 439095 A2 | 7/1991 |
| EP | 2 511 294 A2 | 10/2012 |
| GB | 2188638 A | 10/1987 |
| WO | 85/00974 A1 | 3/1985 |
| WO | 86/01533 A1 | 3/1986 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Ma (Modern Drug Discovery 2004, 7(6)).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Kermer et al (Mol Cancer Ther. Jun. 2012;11(6):1279-88. Epub Apr. 6, 2012).*

(Continued)

Primary Examiner — Brian Gangle
Assistant Examiner — Andrea K McCollum
(74) Attorney, Agent, or Firm — Kagan Binder, PLLC

(57) ABSTRACT

The present invention relates to a pharmaceutical composition for treating a cancer or an infection in a subject by administrating an amount of an interleukin 15 (IL-15) derivative conjugate so as to induce a proliferation of natural killer cells (NK cells) which is the same or higher than the one obtained with high dose of interleukin-2 (HDIL-2); eventually associated with a pharmaceutically acceptable carrier.

28 Claims, 20 Drawing Sheets

Specification includes a Sequence Listing.

(56) References Cited

FOREIGN PATENT DOCUMENTS

| | | |
|---|---|---|
| WO | 95/27722 A1 | 10/1995 |
| WO | 95/30695 A1 | 11/1995 |
| WO | 97/41232 A1 | 11/1997 |
| WO | 2000/047228 A1 | 8/2000 |
| WO | 2001/058957 A2 | 8/2001 |
| WO | 2002/022805 A2 | 3/2002 |
| WO | 2002/072605 A2 | 9/2002 |
| WO | 2003/078334 A1 | 9/2003 |
| WO | 2004/035607 A2 | 4/2004 |
| WO | 2004/035622 A2 | 4/2004 |
| WO | 2005/085282 A1 | 9/2005 |
| WO | 2007046006 A2 | 4/2007 |
| WO | 2007/084342 A2 | 7/2007 |
| WO | 2007/095643 A2 | 8/2007 |
| WO | 2007/128563 A1 | 11/2007 |
| WO | 2008/043777 A1 | 4/2008 |
| WO | 2008/143794 A1 | 11/2008 |
| WO | 2009/002562 A2 | 12/2008 |
| WO | 2009/012600 A1 | 1/2009 |
| WO | 2009/135031 A1 | 11/2009 |
| WO | 2012/175222 A1 | 12/2012 |
| WO | 2012/178137 A1 | 12/2012 |
| WO | 2014/066527 A2 | 5/2014 |

OTHER PUBLICATIONS

Charles River C57BL/6 Mice Data Sheet (downloaded Jun. 18, 2017 from http://www.criver.com/files/pdfs/rms/c57bl6/rm_rm_d_c57bl6n_mouse.aspx).*

HogenEsch et al (J Control Release. Dec. 10, 2012; 164(2): 183-186.) (Year: 2012).*

Bessard et al., "High antitumor activity of RLI, an IL15-IL15Ralpha fusion protein, in metastatic melanoma and colorectal cancer," *Cytokine* 48:91-137 Abstract (1 page) (2009).

Bessard et al., "High antitumor activity of RLI, an interleukin-15 (IL-15)—IL-15 receptor a fusion protein, in metastatic melanoma and colorectal cancer," *Molecular Cancer Therapeutics* 8(9):2736-2745 (Sep. 2009).

Assier, E., et al. (2005). "Constitutive expression of IL-2Rbeta chain and its effects on IL-2-induced vascular leak syndrome." Cytokine 32(6): 280-286.

Kottke, T., et al. (2008). "Treg Depletion-enhanced IL-2 Treatment Facilitates Therapy of Established Tumors Using Systemically Delivered Oncolytic Virus." Molecular Therapy 16(7): 1217-1226.

Fyfe, G., et al. (1995). "Results of treatment of 255 patients with metastatic renal cell carcinoma who received high-lose recombinant interleukin-2 therapy." Journal of Clinical Oncology 13(3): 688-696.

Grabstein, K. H., et al. (1994). "Cloning of a T cell growth factor that interacts with the beta chain of the interleukin-2 receptor." Science 264(5161): 965-968.

Hori, T., et al. (1987). "Establishment of an interleukin 2-dependent human T cell line from a patient with T cell chronic lymphocytic leukemia who is not infected with human T cell leukemia/lymphoma virus." Blood 70(4): 1069-1072.

Smith, T. F. and M. S. Waterman (1981). "Comparison of biosequences." Advances in Applied Mathematics 2(4): 482-489.

Needleman, S. B. and C. D. Wunsch (1970). "A general method applicable to the search for similarities in the amino acid sequence of two proteins." J Mol Biol 48(3): 443-453.

Pearson, W. R. and D. J. Lipman (1988). "Improved tools for biological sequence comparison." Proc Natl Arad Sci U S A 85(8): 2444-2448.

Edgar, R. C. (2004). "MUSCLE: multiple sequence alignment with high accuracy and high throughput." Nucleic Acids Res 32(5): 1792-1797.

Zhu, X., et al. (2009). "Novel human interleukin-15 agonists." Journal of Immunology 183(6): 3598-3607.

Wei, X. et al. (2001). "The Sushi domain of soluble IL-15 receptor alpha is essential for binding IL-15 and inhibiting Inflammatory and allogenic responses in vitro and in vivo." Journal of Immunology 167(1): 277-282.

Murphy, W. J., et al. (2003). "Synergistic anti-tumor responses after administration of agonistic antibodies to CD40 and IL-2: coordination of dendritic and CD8+ cell responses." Journal of Immunology 170(5): 2727-2733.

Itoh, T., et al. (1990). "Antitumor effect of combination of murine recombinant interferon beta, murine recombinant interferon gamma and human recombinant interleukin-2 in MethA-bearing mice." Cancer Immunol Immunother 32(2): 38-94.

Ettinghausen, S. E and S. A. Rosenberg (1986). "Immunotherapy of murine sarcomas using lymphokine activated killer cells: optimization of the schedule and route of administration of recombinant interleukin-2." Cancer Res 46(6): 2784-2792.

Miyara M., et al. (2009). "Functional delineation and differentiation dynamics of human CD4+ T cells expressing the FoxP3 transcription factor." Immunity 30(6): 899-911.

Anderson, D. M., et al. (1995). "Functional characterization of the human interleukin-15 receptor alpha chain and close linkage of IL15RA and IL2RA genes." J Biol Chem 270(50): 29862-29869.

Andersson, L., et al. (2000). "Large-scale synthesis of peptides." Biopolymers 55(3): 227-250.

Avanzi, G. C., et al. (1988). "Selective growth response to IL-3 of a human leukaemic cell line with megakaryoblastic features." Br J Haematol 69(3): 359-366.

Badoual, C., et al. (2008). "The soluble alpha chain of interleukin-15 receptor: a proinflammatory molecule associated with tumor progression in head and neck cancer." Cancer Res 68(10): 3907-3914.

Bamborough, P., et al. (1994). "The interleukin-2 and interleukin-4 receptors studied by molecular modelling." Structure 2(9): 839-851.

Bamford, R. N., et al. (1994). "The interleukin (IL) 2 receptor beta chain is shared by IL-2 and a cytokine, provisionally designated IL-T, that stimulates T-cell proliferation and the induction of lymphokine-activated killer cells." Proc Natl Acad Sci U S A 91(11): 4940-4944.

Bernard, J., et al. (2004). "Identification of an interleukin-15alpha receptor-binding site on human interleukin-15." J Biol Chem 279(23): 24313-24322.

Bouchaud, G., et al. (2008). "The exon-3-encoded domain of IL-15ralpha contributes to IL-15 high-affinity binding and is crucial for the IL-15 antagonistic effect of soluble IL-15Ralpha." J Mol Biol 382(1): 1-12.

Budagian, V., et al. (2004). "Natural soluble interleukin-15R☐ is generated by cleavage that involves the tumor necrosis factor-a-converting enzyme (TACE/ADAM17)." J Biol Chem 279(39): 40368-40375.

Bulanova, E., et al. (2003). "Mast cells express novel functional IL-15 receptor alpha isoforms." J Immunol 170(10): 5045-5055.

Burkett, P. R., et al. (2003). "IL-15Rα expression on CD8+ T cells is dispensable for T cell memory." Proc Natl Acad Sci U S A 100(8): 4724-4729.

Burkett, P. R., et al. (2004). "Coordinate expression and trans presentation of interleukin (IL)-15R☐ and IL-15 supports natural killer cell and memory CD8-+ T cell homeostasis." J Exp Med 200(7): 825-834.

Burton, J. D., et al. (1994). "A lymphokine, provisionally designated interleukin T and produced by a human adult T-cell leukemia line, stimulates T-cell proliferation and the induction of lymphokine-activated killer cells." Proc Natl Acad Sci U S A 91(11): 4935-4939.

Carson, W. E., et al. (1994). "Interleukin (IL) 15 is a novel cytokine that activates human natural killer cells via components of the IL-2 receptor." J Exp Med 180(4): 1395-1403.

Carson, W. and M. A Caligiuri (1998). "Interleukin-15 as a potential regulator of the innate immune response." Braz J Med Biol Res 31(1): 1-9.

Cosman, D., et al. (1995). "Interleukin 15 and its receptor." Ciba Found Symp 195: 221-229; discussion 229-233.

Davis, S., et al. (1993). "Released form of CNTF receptor alpha component as a soluble mediator of CNTF responses." Science 259(5102): 1736-1739.

(56) References Cited

OTHER PUBLICATIONS

De Gast, G. C., et al. (2000). "Phase I trial of combined immunotherapy with subcutaneous granulocyte macrophage colony-stimulating factor, low-dose interleukin 2, and interferon alpha in progressive metastatic melanoma and renal cell carcinoma." Clin Cancer Res 6(4): 1267-1272.
DiSanto, J. P. (1997). "Cytokines: shared receptors, distinct functions." Curr Biol 7(7): R424-426.
Dubois, S., et al. (1999). "Natural splicing of exon 2 of human interleukin-15 receptor alpha-chain mRNA results in a shortened form with a distinct pattern of expression." J Biol Chem 274(38): 26978-26984.
Dubois S. et al (2002). "IL-15Ralpha recycles and presents Il-15 In trans to neighboring cells." Immunity 17(5): 537-547.
Dubois, S., et al. (2008). "Preassociation of IL-15 with IL-15R alpha-IgG1-Fc enhances its activity on proliferation of NK and CD8+/CD44high T cells and its antitumor action." J Immunol 180(4): 2099-2106.
Dudley, M. E and S. A. Rosenberg (2003). "Adoptive-cell-transfer therapy for the treatment of patients with cancer." Nat Rev Cancer 3(9): 666-675.
Eklund, J. W. and T. M. Kuzel (2004). "A review of recent findings involving interleukin-2-based cancer therapy." Curr Opin Oncol 16(6): 542-546.
Elson, G. C., et al. (2000). "CLF associates with CLC to form a functional heteromeric ligand for the CNTF receptor complex." Nat Neurosci 3(9): 867-872.
Farner, N. L., et al. (1997). "Alteration of the CD34+ Tf-1 beta cell line profile in response to long-term exposure to IL-15." Cytokine 9(5): 316-327.
Fernandez-Botran, R. (1991). "Soluble cytokine receptors: their role in immunoregulation." FASEB J 5(11): 2567-2574.
Ferrari-Lacraz, S., et al. (2001). "An antagonist IL-15/Fc protein prevents costimulation blockade-resistant rejection." J Immunol 167(6): 3478-3485.
Ferrari-Lacraz, S., et al. (2004). "Targeting IL-15 receptor-bearing cells with an antagonist mutant IL-15/Fc protein prevents disease development and progression in murine collagen-induced arthritis." J Immunol 173(9): 5818-5826.
Forcina, G., et al. (2004). "Interleukin-15 modulates interferon-gamma and beta-chemokine production in patients with HIV infection: implications for immune-based therapy." Cytokine 25(6): 283-290.
Gerritsen, W. R. (2012). "The evolving role of immunotherapy in prostate cancer." Ann Oncol 23 Suppl 8: viii22-27.
Giri, J. G., et al. (1994). "Utilization of the beta and gamma chains of the IL-2 receptor by the novel cytokine IL-15." EMBO J 13(12): 2822-2830.
Girl, J. G., et al. (1995). "Identification and cloning of a novel IL-15 binding protein that is structurally related to the alpha chain of the IL-2 receptor." EMBO J 14(15): 3654-3663.
Giron-Michel, J., et al. (2005). "Membrane-bound and soluble IL-15/IL-15Ralpha complexes display differential signaling and functions on human hematopoietic progenitors." Blood 106(7): 2302-2310.
Guo, H. and X. Qian (2010). "Clinical applications of adoptive natural killer cell immunotherapy for cancer: current status and future prospects." Onkologie 33(7): 389-395.
Hallett, W. H. and W. J. Murphy (2004). "Natural killer cells: biology and clinical use in cancer therapy." Cell Mol Immunol 1(1): 12-21.
Hammerstrom, A. E., et al. (2011). "Cancer immunotherapy: sipuleucel-T and beyond." Pharmacotherapy 31(8): 813-828.
Heaney, M. L. and D. W. Golde (1998). "Soluble receptors in human disease." J Leukoc Biol 64(2): 135-146.
Hopp, T. P., et al. (1988). "A short polypeptide marker sequence useful for recombinant protein identification and purification." Biotechnology 6(10): 1204-1210.

Huntington, N. D., et al. (2009). "IL-15 trans-presentation promotes human NK cell development and differentiation in vivo." J Exp Med 206(1): 25-34.
Huntington, N. D., et al. (2011). "IL-15 transpresentation promotes both human T-cell reconstitution and T-cell-dependent antibody responses in vivo." Proc Natl Acad Sci U S A 108(15): 6217-6222.
Written Opinion for PCT/IB2006/003917, dated Apr. 20, 2008, 7 pages.
Jones, S. A. and S. Rose-John (2002). "The role of soluble receptors in cytokine biology: the agonistic properties of the sIL-6R/IL-6 complex." Biochim Biophys Acta 1592(3): 251-263.
Kanakura, Y., et al. (1993). "Functional expression of interleukin 2 receptor in a human factor-dependent megakaryoblastic leukemia cell line: evidence that granulocyte-macrophage colony-stimulating factor inhibits interleukin 2 binding to its receptor." Cancer Res 53(3): 675-680.
Karow, J., et al. (1996). "Mediation of interleukin-11-dependent biological responses by a soluble form of the interleukin-11 receptor." Biochem Journal 318 ( Pt 2): 489-495.
Kennedy, M. K. and L. S. Park (1996). "Characterization of interleukin-15 (IL-15) and the Il-15 receptor complex." Jcournal of Clin Immunol 16(3): 134-143.
Kennedy, M. K., et al. (2000). "Reversible defects in natural killer and memory CD8 T cell lineages in interleukin 15-deficient mice." J Exp Med 191(5): 771-780.
Kobayashi, H., et al. (2005). "Role of trans-cellular IL-15 presentation in the activation of NK cell-mediated killing, which leads to enhanced tumor immunosurveillance." Blood 105(2): 721-727.
Koka, R., et al (2003). "Interleukin (IL)-15Ra-deficient natural killer cells survive in normal but not IL-15Ra-deficient mice." J Exp Med 197(8): 977-984.
Ku, C. C., et al. (2000). "Control of homeostasis of CD8+ memory T cells by opposing cytokines." Science 288(5466): 675-678.
Lehours, P., et al. (2000). "Subunit structure of the high and low affinity human interleukin-15 receptors." Eur Cytokine Netw 11(2): 207-215.
Li, X. C., et al. (2001). "IL-15 and IL-2: a matter of life and death for T cells in vivo." Nat Med 7(1): 114-118.
Liu, K., et al. (2002). "IL-15 mimics T cell receptor crosslinking in the induction of cellular proliferation, gene expression, and cytotoxicity in CD8+ memory T cells." Proc Natl Acad Sci U S A 99(9): 6192-6197.
Lodolce, J. P., et al. (1998). "IL-15 receptor maintains lymphoid homeostasis by supporting lymphocyte homing and proliferation." Immunity 9(5): 669-676.
Lodolce, J. P., et al. (2001). "T cell-independent interleukin 15Ralpha signals are required for bystander proliferation." J Exp Med 194(8): 1187-1194.
Lorenzen, I., et al. (2006). "The structure of the interleukin-15 alpha receptor and its implications for ligand binding." J Biol Chem 281(10): 6642-6647.
Margolin, K. A. (2000). "Interleukin-2 in the treatment of renal cancer." Semin Oncol 27(2): 194-203.
Marks-Konczalik, J., et al. (2000). "IL-2-induced activation-induced cell death is inhibited in IL-15 transgenic mice." Proc Natl Acad Sci U S A 97(21): 11445-11450.
Matsumoto, M., et al. (2003). "On-column refolding and characterization of soluble human interleukin-15 receptor alpha-chain produced in *Escherichia coli*." Protein Expr Purif 31(1): 64-71.
Meazza R., et al. (2011). "Role of common-gamma chain cytokines in NK cell development and function: perspectives for immunotherapy." J Biomed Biotechnol 2011: 861920.
Meissner, U., et al. (2001). "A soluble form of the murine common gamma chain is present at high concentrations in vivo and suppresses cytokine signaling." Blood 97(1): 183-191.
Mortier, E., et al. (2004). "Natural, proteolytic release of a soluble form of human IL-15 receptor alpha-chain that behaves as a specific, high affinity IL-15 antagonist." J Immunol 173(3): 1681-1688.
Mortier, E., et al. (2006). "Soluble interleukin-15 receptor alpha (IL-15R alpha)-sushi as a selective and potent agonist of IL-15 action through IL-15R beta/gamma. Hyperagonist IL-15 x IL-15R alpha fusion proteins." J Biol Chem 281(3): 1612-1619.

(56) References Cited

OTHER PUBLICATIONS

Nakamura, Y., et al. (1994). "Heterodimerization of the IL-2 receptor beta- and gamma-chain cytoplasmic domains is required for signalling." Nature 369(6478): 330-333.
Neely, G. G., et al. (2004). "Monocyte surface-bound IL-15 can function as an activating receptor and participate in reverse signaling." J Immunol 172(7): 4225-4234.
Norman, D. G., et al. (1991). "Three-dimensional structure of a complement control protein module in solution." J Mol Biol 219(4): 717-725.
Oh, S., et al. (2004). "IL-15/IL-15Ralpha-mediated avidity maturation of memory CD8+ T cells." Proc Natl Acad Sci U S A 101(42): 15154-15159.
Ohteki, T., et al. (1997). "Role for IL-15/IL-15 receptor beta-chain in natural killer 1.1+ T cell receptor-alpha beta+ cell development." J Immunol 159(12): 5931-5935.
Olosz, F. and T. R. Malek (2002). "Structural basis for binding multiple ligands by the common cytokine receptor gamma-chain." J Biol Chem 277(14): 12047-12052.
Pereno, R., et al. (1999). "IL-15/IL-15R alpha intracellular trafficking in human cells and protection from apoptosis." Ann N Y Acad Sci 876: 236-245.
Pettit, D. K., et al. (1997). "Structure-function studies of interleukin 15 using site-specific mutagenesis, polyethylene glycol conjugation, and homology modeling." J Biol Chem 272(4): 2312-2318.
Pflanz, S., et al. (1999). "A fusion protein of interleukin-11 and soluble interleukin-11 receptor acts as a superagonist on cells expressing gp130." FEBS Lett 450(1-2): 117-122.
Plautz, G. E., et al. (2003). "Considerations on clinical use of T cell immunotherapy for cancer." Arch Immunol Ther Exp (Warsz) 51(4): 245-257.
Prinz, M., et al. (1998). "Alternative splicing of mouse IL-15 is due to the use of an internal splice site in exon 5." Brain Res Mol Brain Res 63(1): 155-162.
Quemener, A., et al. (2006). "Docking of human interleukin-15 to its specific receptor alpha chain: correlation between molecular modeling and mutagenesis experimental data." Proteins 65(3): 623-636.
Rose, T., et al. (2003). "Structural analysis and modeling of a synthetic interleukin-2 mimetic and its interleukin-2Rbeta2 receptor." J Biol Chem 278(25): 22868-22876.
Rose-John, S. and P. C. Heinrich (1994). "Soluble receptors for cytokines and growth factors: generation and biological function." Biochem J 300 ( Pt 2): 281-290.
Rosenberg, S. A., et al. (1994). "Treatment of patients with metastatic melanoma with autologous tumor-infiltrating lymphocytes and interleukin 2." J Natl Cancer Inst 86(15): 1159-1166.
Rubinstein, M. P., et al. (2006). "Converting IL-15 to a superagonist by binding to soluble IL-15R☐." Proc Natl Acad Sci U S A 103(24): 9166-9171.
Ruchatz, H., et al. (1998). "Soluble IL-15 receptor alpha-chain administration prevents murine collagen-induced arthritis: a role for IL-15 in development of antigen-induced immunopathology." J Immunol 160(11): 5654-5660.
Ruggeri, L., et al. (2002). "Effectiveness of donor natural killer cell alloreactivity in mismatched hematopoietic transplants." Science 295(5562): 2097-2100.
Sandau, M. M., et al. (2004). "Cutting edge: transpresentation of IL-15 by bone marrow-derived cells necessitates expression of IL-15 and IL-15R alpha by the same cells." J Immunol 173(11): 6537-6541.
Scheller, J. and S. Rose-John (2006). "Interleukin-6 and its receptor: from bench to bedside." Med Microbiol Immunol 195(4): 173-183.
Schluns, K. S., et al. (2004). "Distinct cell types control lymphoid subset development by means of IL-15 and IL-15 receptor alpha expression." Proc Natl Arad Sci U S A 101(15): 5616-5621.
Schulz, O., et al. (1998). "Proteolytic cleavage of CD25, the alpha subunit of the human T cell interleukin 2 receptor, by Der p. 1, a major mite allergen with cysteine protease activity." J Exp Med 187(2): 271-275.

Sheu, B. C., et al. (2001). "A novel role of metalloproteinase in cancer-mediated immunosuppression." Cancer Res 61 (1): 237-242.
Smith, X. G., et al. (2000). "Selective blockade of IL-15 by soluble IL-15 receptor alpha-chain enhances cardiac allograft survival." J Immunol 165(6): 3444-3450.
Stoklasek, T. A., et al. (2006). "Combined IL-15/IL-15Ralpha immunotherapy maximizes IL-15 activity in vivo." J Immunol 177(9): 6072-6080.
Van Belle, T. and J. Grooten (2005). "IL-15 and IL-15Ralpha in CD4+T cell immunity." Arch Immunol Ther Exp (Warsz) 53(2): 115-126.
Waldmann, T., et al. (1998). "Interleukin-2, interleukin-15, and their receptors." Int Rev Immunol 16(3-4): 205-226.
Waldmann, T. A (2002). "The IL-2/IL-15 receptor systems: targets for immunotherapy." J Clin Immunol 22(2): 51-56.
Walzer, T., et al. (2007). "Natural killer cell trafficking in vivo requires a dedicated sphingosine 1-phosphate receptor." Nat Immunol 8(12): 1337-1344.
Wilkinson, P. C. and F. Y. Liew (1995). "Chemoattraction of human blood T lymphocytes by interleukin-15." J Exp Med 181(3): 1255-1259.
Allegra, C. J., et al. (2011). "Phase III trial assessing bevacizumab in stages II and III carcinoma of the colon: results of NSABP protocol C-08." J Clin Oncol 29(1): 11-16.
Baker, M. & Carr, F. 2010. Pre-clinical considerations in the assessment of immunogenicity for protein therapeutics. Curr Drug Saf, 5, 308-13.
Kaspar, M., et al. (2007). "The antibody-mediated targeted delivery of interleukin-15 and GM-CSF to the tumor neovasculature inhibits tumor growth and metastasis." Cancer Res 67(10): 4940-4948.
Kermer, V., et al. (2010). Antibody fusion proteins for cancer immunotherapy mimicking IL-15 trans presentation at the tumor site. CIMT Cancer Immunotherapy 8th annual meeting, CIMT abstract book 2010: abstract No. 113, 163.
Lode, H. N. and R. A. Reisfeld (2000). "Targeted cytokines for cancer immunotherapy." Immunol Res 21(2-3): 279-288.
Lode, H. N., et al. (1997). "Targeted interleukin-2 therapy for spontaneous neuroblastoma metastases to bone marrow." J Natl Cancer Inst 89(21): 1586-1594.
Riechmann, L., et al. (1988). "Reshaping human antibodies for therapy." Nature 332(6162): 323-327.
Ronca, R., et al. (2009). "Delivering cytokines at tumor site: The immunocytokine-conjugated anti-EDB-fibronectin antibody case." Immunobiology 214(9-10): 800-810.
Scott, A. M., et al. (2012). "Antibody therapy of cancer." Nat Rev Cancer 12(4): 278-287.
Singh, H., et al. (2007). "Combining adoptive cellular and immunocytokine therapies to improve treatment of B-lineage malignancy." Cancer Res 67(6): 2872-2880.
Stone, J.D., (2012) "Design Characterization of a protein superagonist of IL-15 fused with IL-15Ralpha and high-affinity T cell receptor", Biotechnol. Prog., 28(6):1588-1597.
Stone et al., "Design and characterization of a protein superagonist of IL-15 fused with IL-15Rα and a high-affinity T cell receptor", Biotechnol Prog., 28(6), Nov. 2012, pp. 1588-1597.
Notice of Refusal for Japanese Application No. 2016-508046, dated Jan. 23, 2018, 8 pages.
Yu et al. (2010) "Simultaneous Blockade of Multiple Immune System Inhibitory Checkpoints Enhances Antitumor Activity Mediated by Interleukin-15 in a Murine Metastatic Colon Carcinoma Model", Clinical Cancer Research, 16 (24):6019-6028.
Vincent et al. (2013) "Tumor targeting of the IL-15 superagonist RLI by an anti-GD2 antibody strongly enhances its antitumor potency", International Journal of Cancer, 133:757-765.
Vincent et al. (2011) "Development of two IL15 immunocytokines targeting either GD2- or CD20- tumoral bearing cells", Cytokinem 56, p. 102 (Abstract).
Xu et al. (2013) "Efficacy and Mechanism-of-Action of a Novel Superagonist Interleukin-15: Interleukin-15 Receptor aSu/Fc Fusion Complex in Syngeneic Murine Models of Multiple Myeloma", Cancer Research, 73(10):3075-3086 Supplementary Material, pp. 1-4).

(56) References Cited

OTHER PUBLICATIONS

Xu et al. (2012) "The tumor immunosuppressive microenvironment impairs the therapy of anti-HER2/neu antibody", Protien Cells, 3(6):441-449.
Bessard et al. (2009) "High antitumor activity of RU, an interleukin-15 (Il-15)-IL-15 receptor a fusion protein, in metastatic melanoma and colorectal cancer", Molecular Cancer Therapeutics, 8(9):2736-2745.
Kermer et al. (2012) "An Antibody Fusion Protein for Cancer Immunotherapy Mimicking IL-15 trans-Presentation at the Tumor Site" Molecular Cancer Therapeutics, 11(6):1279-1288.
Yu et al. (2012) "Simultaneous inhibition of two regulatory T-cell subsets enhanced Interleukin-15 efficacy in a prostate tumor model", PNAS, 10-(16):6187-6192.
Mortier et al (2006) "Soluble Interleukin-15 Receptor a (IL-1 SRa)-sushi as a Selective and Potent Agonist of IL-15 Action through IL-15R beta/gamma", The Journal of Biological Chemistry, 281(3):1612-1619.
"PubChem Record Pidilizumab", SID 223366026—PubChem, IUPHAR/BPS Guide to Pharmacology, Nov. 13, 2014, 6 pages.
"Pidilizumab Report", IUPHAR/BPS Guide lo Pharmacology, Mar. 26, 2020, 2 pages.
"SEC submission from Medivation", U.S. Securities and Exchange Commission, Form 8-K, Medivation, Inc., Jan. 25, 2016, 4 pages.
Stenner et al. (2018) "Cancer Immunotherapy and the Immune Response in Follicular Lymphoma", Frontiers in Oncology, 8(219):1-7.
Vonderhelde et al. (2013) "Agonistic CD40 antibodies and cancer therapy", Clin. Cancer Res., 19(5):1035-1043.
Drew M. Pardoll (2012) "The blockade of immune checkpoints in cancer immunotherapy", Nature, 12:252-264.
Capece et al. (2012) "Targeting Costimulatory Molecules to Improve Antitumor Immunity", Journal of Biomedicine and Biotechnology, pp. 1-17.
Hamid et al. (2013) "Safety and Tumor Responses with Lambrolizumab (Anti-PD-1) in Melanoma", The New England Journal of Medicine, 369(2):134-144.
"Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001)", ClinicalTrials.gov Identifier: NCT01295827, Feb. 15, 2011, 23 pages.
Fischer, et al. (1997) "A bioactive designer cytokine for human hematopoietic progenitor cell expansion", Nature Biotechnology, 15:142-145.
"Guidance for Industry—Estimating the Maximum Safe Starting Dose in Initial Clinical Trials for Therapeutics in Adult Healthy Volunteers", Pharmacology and Toxicology, Jul. 2005, 30 pages.

\* cited by examiner

SEQUENCE LISTING

```
<160> NUMBER OF SEQ ID NOS: 18

<210> SEQ ID NO 1
<211> LENGTH: 114
<212> TYPE: PRT
<213> ORGANISM: artificial sequence
<220> FEATURE:
<223> OTHER INFORMATION: mammalian interleukin 15 consensus sequence
<220> FEATURE:
<221> NAME/KEY: MISC_FEATURE
<222> LOCATION: (1)..(1)
<223> OTHER INFORMATION: X= N, S, T or I
<220> FEATURE:
<221> NAME/KEY: MISC_FEATURE
<222> LOCATION: (3)..(3)
<223> OTHER INFORMATION: X= V, H, I, Q or E
<220> FEATURE:
<221> NAME/KEY: MISC_FEATURE
<222> LOCATION: (4)..(4)
<223> OTHER INFORMATION: X= N, Y, F or D
<220> FEATURE:
<221> NAME/KEY: MISC_FEATURE
<222> LOCATION: (6)..(6)
<223> OTHER INFORMATION: X= I or R
<220> FEATURE:
<221> NAME/KEY: MISC_FEATURE
<222> LOCATION: (7)..(7)
<223> OTHER INFORMATION: X= S, N, L, Y, K or R
<220> FEATURE:
<221> NAME/KEY: MISC_FEATURE
<222> LOCATION: (10)..(10)
<223> OTHER INFORMATION: X= K, E, R or Q
<220> FEATURE:
<221> NAME/KEY: MISC_FEATURE
<222> LOCATION: (11)..(11)
<223> OTHER INFORMATION: X= K, T or R
<220> FEATURE:
<221> NAME/KEY: MISC_FEATURE
<222> LOCATION: (13)..(13)
<223> OTHER INFORMATION: X= E, D or Q
<220> FEATURE:
<221> NAME/KEY: MISC_FEATURE
<222> LOCATION: (14)..(14)
<223> OTHER INFORMATION: X= D, H, S or N
<220> FEATURE:
<221> NAME/KEY: MISC_FEATURE
<222> LOCATION: (16)..(16)
<223> OTHER INFORMATION: X= I or T
<220> FEATURE:
<221> NAME/KEY: MISC_FEATURE
<222> LOCATION: (17)..(17)
<223> OTHER INFORMATION: X=Q, R or K
<220> FEATURE:
<221> NAME/KEY: MISC_FEATURE
<222> LOCATION: (18)..(18)
<223> OTHER INFORMATION: X= S or F
```

-continued

```
<220> FEATURE:
<221> NAME/KEY: MISC_FEATURE
<222> LOCATION: (19)..(19)
<223> OTHER INFORMATION: X= M, I or L
<220> FEATURE:
<221> NAME/KEY: MISC_FEATURE
<222> LOCATION: (21)..(21)
<223> OTHER INFORMATION: X= I, V or M
<220> FEATURE:
<221> NAME/KEY: MISC_FEATURE
<222> LOCATION: (23)..(23)
<223> OTHER INFORMATION: X=A or T
<220> FEATURE:
<221> NAME/KEY: MISC_FEATURE
<222> LOCATION: (28)..(28)
<223> OTHER INFORMATION: X=E or D
<220> FEATURE:
<221> NAME/KEY: MISC_FEATURE
<222> LOCATION: (30)..(30)
<223> OTHER INFORMATION: X= D or G
<220> FEATURE:
<221> NAME/KEY: MISC_FEATURE
<222> LOCATION: (31)..(31)
<223> OTHER INFORMATION: X= V, F, A or I
<220> FEATURE:
<221> NAME/KEY: MISC_FEATURE
<222> LOCATION: (34)..(34)
<223> OTHER INFORMATION: X= S, N or R
<220> FEATURE:
<221> NAME/KEY: MISC_FEATURE
<222> LOCATION: (37)..(37)
<223> OTHER INFORMATION: X= V or I
<220> FEATURE:
<221> NAME/KEY: MISC_FEATURE
<222> LOCATION: (39)..(39)
<223> OTHER INFORMATION: X= A or T
<220> FEATURE:
<221> NAME/KEY: MISC_FEATURE
<222> LOCATION: (41)..(41)
<223> OTHER INFORMATION: X= K, Q or N
<220> FEATURE:
<221> NAME/KEY: MISC_FEATURE
<222> LOCATION: (48)..(48)
<223> OTHER INFORMATION: X= Q, G, R, H or E
<220> FEATURE:
<221> NAME/KEY: MISC_FEATURE
<222> LOCATION: (51)..(51)
<223> OTHER INFORMATION: X= S or L
<220> FEATURE:
<221> NAME/KEY: MISC_FEATURE
<222> LOCATION: (52)..(52)
<223> OTHER INFORMATION: X= L, Q or H
<220> FEATURE:
<221> NAME/KEY: MISC_FEATURE
<222> LOCATION: (54)..(54)
<223> OTHER INFORMATION: X= S, F or Y
<220> FEATURE:
<221> NAME/KEY: MISC_FEATURE
<222> LOCATION: (55)..(55)
<223> OTHER INFORMATION: X= G, K, S, N or R
<220> FEATURE:
<221> NAME/KEY: MISC_FEATURE
<222> LOCATION: (56)..(56)
<223> OTHER INFORMATION: X= D, H, S or N
<220> FEATURE:
<221> NAME/KEY: MISC_FEATURE
<222> LOCATION: (57)..(57)
<223> OTHER INFORMATION: X= A, H, M, E, G, S or T
<220> FEATURE:
<221> NAME/KEY: MISC_FEATURE
<222> LOCATION: (58)..(58)
<223> OTHER INFORMATION: X= S, V, P, T, N or D
<220> FEATURE:
<221> NAME/KEY: MISC_FEATURE
<222> LOCATION: (59)..(59)
<223> OTHER INFORMATION: X= I or L
<220> FEATURE:
<221> NAME/KEY: MISC_FEATURE
<222> LOCATION: (60)..(60)
```

```
<223> OTHER INFORMATION: X=  H, S, K, N, Y or E
<220> FEATURE:
<221> NAME/KEY: MISC_FEATURE
<222> LOCATION: (61)..(61)
<223> OTHER INFORMATION: X=  D or E
<220> FEATURE:
<221> NAME/KEY: MISC_FEATURE
<222> LOCATION: (62)..(62)
<223> OTHER INFORMATION: X=  T, I or A
<220> FEATURE:
<221> NAME/KEY: MISC_FEATURE
<222> LOCATION: (63)..(63)
<223> OTHER INFORMATION: X=  V or I
<220> FEATURE:
<221> NAME/KEY: MISC_FEATURE
<222> LOCATION: (64)..(64)
<223> OTHER INFORMATION: X=  E, T, Q, R or K
<220> FEATURE:
<221> NAME/KEY: MISC_FEATURE
<222> LOCATION: (66)..(66)
<223> OTHER INFORMATION: X=  L or V
<220> FEATURE:
<221> NAME/KEY: MISC_FEATURE
<222> LOCATION: (67)..(67)
<223> OTHER INFORMATION: X=  I, T or L
<220> FEATURE:
<221> NAME/KEY: MISC_FEATURE
<222> LOCATION: (68)..(68)
<223> OTHER INFORMATION: X=I, M, F, Y or L
<220> FEATURE:
<221> NAME/KEY: MISC_FEATURE
<222> LOCATION: (72)..(72)
<223> OTHER INFORMATION: X=  N, T, R, D or S
<220> FEATURE:
<221> NAME/KEY: MISC_FEATURE
<222> LOCATION: (73)..(73)
<223> OTHER INFORMATION: X=  S, N, R, T or I
<220> FEATURE:
<221> NAME/KEY: MISC_FEATURE
<222> LOCATION: (75)..(75)
<223> OTHER INFORMATION: X=  S or N
<220> FEATURE:
<221> NAME/KEY: MISC_FEATURE
<222> LOCATION: (76)..(76)
<223> OTHER INFORMATION: X=  S or A
<220> FEATURE:
<221> NAME/KEY: MISC_FEATURE
<222> LOCATION: (77)..(77)
<223> OTHER INFORMATION: X=  N, I or K
<220> FEATURE:
<221> NAME/KEY: MISC_FEATURE
<222> LOCATION: (78)..(78)
<223> OTHER INFORMATION: X=  G, E or K
<220> FEATURE:
<221> NAME/KEY: MISC_FEATURE
<222> LOCATION: (79)..(79)
<223> OTHER INFORMATION: X=  N, Y, D or T
<220> FEATURE:
<221> NAME/KEY: MISC_FEATURE
<222> LOCATION: (80)..(80)
<223> OTHER INFORMATION: X=  V, K or I
<220> FEATURE:
<221> NAME/KEY: MISC_FEATURE
<222> LOCATION: (81)..(81)
<223> OTHER INFORMATION: X=  T, A or I
<220> FEATURE:
<221> NAME/KEY: MISC_FEATURE
<222> LOCATION: (83)..(83)
<223> OTHER INFORMATION: X=  S, L or T
<220> FEATURE:
<221> NAME/KEY: MISC_FEATURE
<222> LOCATION: (87)..(87)
<223> OTHER INFORMATION: X=  E or V
<220> FEATURE:
<221> NAME/KEY: MISC_FEATURE
<222> LOCATION: (93)..(93)
<223> OTHER INFORMATION: X=  E or K
<220> FEATURE:
<221> NAME/KEY: MISC_FEATURE
```

```
<222> LOCATION: (94)..(94)
<223> OTHER INFORMATION: X= K or R
<220> FEATURE:
<221> NAME/KEY: MISC_FEATURE
<222> LOCATION: (95)..(95)
<223> OTHER INFORMATION: X= N, T or S
<220> FEATURE:
<221> NAME/KEY: MISC_FEATURE
<222> LOCATION: (96)..(96)
<223> OTHER INFORMATION: X= I or F
<220> FEATURE:
<221> NAME/KEY: MISC_FEATURE
<222> LOCATION: (97)..(97)
<223> OTHER INFORMATION: X= K, N, A, or T
<220> FEATURE:
<221> NAME/KEY: MISC_FEATURE
<222> LOCATION: (101)..(101)
<223> OTHER INFORMATION: X= Q, K or E
<220> FEATURE:
<221> NAME/KEY: MISC_FEATURE
<222> LOCATION: (104)..(104)
<223> OTHER INFORMATION: X= V, I or K
<220> FEATURE:
<221> NAME/KEY: MISC_FEATURE
<222> LOCATION: (105)..(105)
<223> OTHER INFORMATION: X= H or R
<220> FEATURE:
<221> NAME/KEY: MISC_FEATURE
<222> LOCATION: (112)..(112)
<223> OTHER INFORMATION: X= N or Y
<220> FEATURE:
<221> NAME/KEY: MISC_FEATURE
<222> LOCATION: (113)..(113)
<223> OTHER INFORMATION: X= = T, S, P, L or A
<220> FEATURE:
<221> NAME/KEY: MISC_FEATURE
<222> LOCATION: (114)..(114)
<223> OTHER INFORMATION: X= = S or P

<400> SEQUENCE: 1

Xaa Trp Xaa Xaa Val Xaa Xaa Asp Leu Xaa Xaa Ile Xaa Xaa Leu Xaa
1               5                   10                  15

Xaa Xaa Xaa His Xaa Asp Xaa Thr Leu Tyr Thr Xaa Ser Xaa Xaa His
            20                  25                  30

Pro Xaa Cys Lys Xaa Thr Xaa Met Xaa Cys Phe Leu Leu Glu Leu Xaa
        35                  40                  45

Val Ile Xaa Xaa Glu Xaa Xaa Xaa Xaa Xaa Xaa Xaa Xaa Xaa Xaa Xaa
    50                  55                  60

Asn Xaa Xaa Xaa Leu Ala Asn Xaa Xaa Leu Xaa Xaa Xaa Xaa Xaa Xaa
65                  70                  75                  80

Xaa Glu Xaa Gly Cys Lys Xaa Cys Glu Glu Leu Glu Xaa Xaa Xaa Xaa
                85                  90                  95

Xaa Glu Phe Leu Xaa Ser Phe Xaa Xaa Ile Val Gln Met Phe Ile Xaa
            100                 105                 110

Xaa Xaa

<210> SEQ ID NO 2
<211> LENGTH: 114
<212> TYPE: PRT
<213> ORGANISM: Artificial Sequence
<220> FEATURE:
<223> OTHER INFORMATION: primate uinterleukin 15 consensus sequence
<220> FEATURE:
<221> NAME/KEY: MISC_FEATURE
<222> LOCATION: (1)..(1)
<223> OTHER INFORMATION: X = N or I
<220> FEATURE:
<221> NAME/KEY: MISC_FEATURE
<222> LOCATION: (4)..(4)
<223> OTHER INFORMATION: X = N or D
```

-continued

```
<220> FEATURE:
<221> NAME/KEY: MISC_FEATURE
<222> LOCATION: (10)..(10)
<223> OTHER INFORMATION: X = K or R
<220> FEATURE:
<221> NAME/KEY: MISC_FEATURE
<222> LOCATION: (11)..(11)
<223> OTHER INFORMATION: X = K or R
<220> FEATURE:
<221> NAME/KEY: MISC_FEATURE
<222> LOCATION: (13)..(13)
<223> OTHER INFORMATION: X = E or Q
<220> FEATURE:
<221> NAME/KEY: MISC_FEATURE
<222> LOCATION: (16)..(16)
<223> OTHER INFORMATION: X = I or T
<220> FEATURE:
<221> NAME/KEY: MISC_FEATURE
<222> LOCATION: (19)..(19)
<223> OTHER INFORMATION: X = M or I
<220> FEATURE:
<221> NAME/KEY: MISC_FEATURE
<222> LOCATION: (30)..(30)
<223> OTHER INFORMATION: X = D or G
<220> FEATURE:
<221> NAME/KEY: MISC_FEATURE
<222> LOCATION: (31)..(31)
<223> OTHER INFORMATION: X = V or I
<220> FEATURE:
<221> NAME/KEY: MISC_FEATURE
<222> LOCATION: (34)..(34)
<223> OTHER INFORMATION: X = S or R
<220> FEATURE:
<221> NAME/KEY: MISC_FEATURE
<222> LOCATION: (52)..(52)
<223> OTHER INFORMATION: X = L or H
<220> FEATURE:
<221> NAME/KEY: MISC_FEATURE
<222> LOCATION: (55)..(55)
<223> OTHER INFORMATION: X = G or N
<220> FEATURE:
<221> NAME/KEY: MISC_FEATURE
<222> LOCATION: (56)..(56)
<223> OTHER INFORMATION: X = D or N
<220> FEATURE:
<221> NAME/KEY: MISC_FEATURE
<222> LOCATION: (57)..(57)
<223> OTHER INFORMATION: X = A or T
<220> FEATURE:
<221> NAME/KEY: MISC_FEATURE
<222> LOCATION: (58)..(58)
<223> OTHER INFORMATION: X = S, N or D
<220> FEATURE:
<221> NAME/KEY: MISC_FEATURE
<222> LOCATION: (60)..(60)
<223> OTHER INFORMATION: X = H or N
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (67)..(67)
<223> OTHER INFORMATION: X = I or L
<220> FEATURE:
<221> NAME/KEY: MISC_FEATURE
<222> LOCATION: (72)..(72)
<223> OTHER INFORMATION: X = N or R
<220> FEATURE:
<221> NAME/KEY: MISC_FEATURE
<222> LOCATION: (73)..(73)
<223> OTHER INFORMATION: X =S or I
<220> FEATURE:
<221> NAME/KEY: MISC_FEATURE
<222> LOCATION: (76)..(76)
<223> OTHER INFORMATION: X =S or A
<220> FEATURE:
<221> NAME/KEY: MISC_FEATURE
<222> LOCATION: (79)..(79)
```

```
<223> OTHER INFORMATION: X =N or T
<220> FEATURE:
<221> NAME/KEY: MISC_FEATURE
<222> LOCATION: (80)..(80)
<223> OTHER INFORMATION: X =V or I
<220> FEATURE:
<221> NAME/KEY: MISC_FEATURE
<222> LOCATION: (93)..(93)
<223> OTHER INFORMATION: X =E or K
<220> FEATURE:
<221> NAME/KEY: MISC_FEATURE
<222> LOCATION: (112)..(112)
<223> OTHER INFORMATION: X = N or Y
<220> FEATURE:
<221> NAME/KEY: MISC_FEATURE
<222> LOCATION: (113)..(113)
<223> OTHER INFORMATION: X = T or A

<400> SEQUENCE: 2

Xaa Trp Val Xaa Val Ile Ser Asp Leu Xaa Xaa Ile Xaa Asp Leu Xaa
1               5                   10                  15

Gln Ser Xaa His Ile Asp Ala Thr Leu Tyr Thr Glu Ser Xaa Xaa His
            20                  25                  30

Pro Xaa Cys Lys Val Thr Ala Met Lys Cys Phe Leu Leu Glu Leu Gln
        35                  40                  45

Val Ile Ser Xaa Glu Ser Xaa Xaa Xaa Ile Xaa Asp Thr Xaa Glu
50                  55                  60

Asn Leu Xaa Ile Leu Ala Asn Xaa Xaa Leu Ser Xaa Asn Gly Xaa Xaa
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Xaa
            100                 105                 110

Xaa Ser

<210> SEQ ID NO 3
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: X= E or K

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Asn
            100                 105                 110

Thr Ser
```

-continued

```
<210> SEQ ID NO 4
<211> LENGTH: 61
<212> TYPE: PRT
<213> ORGANISM: Artificial Sequence
<220> FEATURE:
<223> OTHER INFORMATION: mammalian sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (7)..(7)
<223> OTHER INFORMATION: X= V or I
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (16)..(16)
<223> OTHER INFORMATION: X= S or N
<220> FEATURE:
<221> NAME/KEY: MISC_FEATURE
<222> LOCATION: (19)..(19)
<223> OTHER INFORMATION: X= L or V
<220> FEATURE:
<221> NAME/KEY: MISC_FEATURE
<222> LOCATION: (20)..(20)
<223> OTHER INFORMATION: X= Y, H or N
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (39)..(39)
<223> OTHER INFORMATION: X= S or T
<220> FEATURE:
<221> NAME/KEY: MISC_FEATURE
<222> LOCATION: (41)..(41)
<223> OTHER INFORMATION: X=T or I
<220> FEATURE:
<221> NAME/KEY: MISC_FEATURE
<222> LOCATION: (45)..(45)
<223> OTHER INFORMATION: X=T or I
<220> FEATURE:
<221> NAME/KEY: MISC_FEATURE
<222> LOCATION: (45)..(45)
<223> OTHER INFORMATION: X= L or I
<220> FEATURE:
<221> NAME/KEY: MISC_FEATURE
<222> LOCATION: (48)..(48)
<223> OTHER INFORMATION: X= A or N
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= H or Y

<400> SEQUENCE: 4

Cys Pro Xaa Pro Xaa Ser Xaa Glu His Ala Asp Ile Xaa Val Lys Xaa
 1               5                  10                  15

Tyr Ser Xaa Xaa Ser Arg Glu Arg Tyr Xaa Cys Asn Ser Gly Phe Lys
            20                  25                  30

Arg Lys Ala Gly Thr Ser Xaa Leu Xaa Glu Cys Val Xaa Asn Lys Xaa
        35                  40                  45
```

```
        Thr Asn Xaa Ala Xaa Trp Thr Thr Pro Ser Leu Lys Cys
         50              55                  60
```

```
<210> SEQ ID NO 5
<211> LENGTH: 64
<212> TYPE: PRT
<213> ORGANISM: Artificial Sequence
<220> FEATURE:
<223> OTHER INFORMATION: enlarged mammalian sushi domain consensus
      sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X=L or V
<220> FEATURE:
<221> NAME/KEY: MISC_FEATURE
<222> LOCATION: (22)..(22)
<223> OTHER INFORMATION: X=Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X= A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y

<400> SEQUENCE: 5

Xaa Thr Cys Pro Xaa Pro Xaa Ser Xaa Glu His Ala Asp Ile Xaa Val
1               5                   10                  15
```

```
Lys Xaa Tyr Ser Xaa Xaa Ser Arg Glu Arg Tyr Xaa Cys Asn Ser Gly
         20              25                  30

Phe Lys Arg Lys Ala Gly Thr Ser Xaa Leu Xaa Glu Cys Val Xaa Asn
         35              40                  45

Lys Xaa Thr Asn Xaa Ala Xaa Trp Thr Thr Pro Ser Leu Lys Cys Ile
         50              55                  60
```

<210> SEQ ID NO 6
<211> LENGTH: 61
<212> TYPE: PRT
<213> ORGANISM: Artificial Sequence
<220> FEATURE:
<223> OTHER INFORMATION: primate sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (20)..(20)
<223> OTHER INFORMATION: X= Y or H
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= V or A

<400> SEQUENCE: 6

```
Cys Pro Xaa Pro Xaa Ser Val Glu His Ala Asp Ile Xaa Val Lys Ser
1               5                   10                  15

Tyr Ser Leu Xaa Ser Arg Glu Arg Tyr Xaa Cys Asn Ser Gly Phe Lys
             20              25                  30

Arg Lys Ala Gly Thr Ser Ser Leu Thr Glu Cys Val Leu Asn Lys Ala
         35              40                  45

Thr Asn Xaa Ala Xaa Trp Thr Thr Pro Ser Leu Lys Cys
         50              55                  60
```

<210> SEQ ID NO 7
<211> LENGTH: 63
<212> TYPE: PRT
<213> ORGANISM: Artificial Sequence
<220> FEATURE:
<223> OTHER INFORMATION: enlarged primate sushi domain consensus
      sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)

```
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X=V or A
<220> FEATURE:
<221> NAME/KEY: MISC_FEATURE
<222> LOCATION: (55)..(55)
<223> OTHER INFORMATION: X=H or Y

<400> SEQUENCE: 7

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys
    50                  55                  60

<210> SEQ ID NO 8
<211> LENGTH: 61
<212> TYPE: PRT
<213> ORGANISM: Homo sapiens

<400> SEQUENCE: 8

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
    50                  55                  60

<210> SEQ ID NO 9
<211> LENGTH: 64
<212> TYPE: PRT
<213> ORGANISM: Homo sapiens

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

<210> SEQ ID NO 10
<211> LENGTH: 77
```

```
<212> TYPE: PRT
<213> ORGANISM: Artificial Sequence
<220> FEATURE:
<223> OTHER INFORMATION: mammalian sushi and domains consensus sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X= L or V
<220> FEATURE:
<221> NAME/KEY: MISC_FEATURE
<222> LOCATION: (22)..(22)
<223> OTHER INFORMATION: X= Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X=A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X=A, S or L
<220> FEATURE:
<221> NAME/KEY: MISC_FEATURE
<222> LOCATION: (70)..(70)
<223> OTHER INFORMATION: X= V, A, S or T
<220> FEATURE:
<221> NAME/KEY: MISC_FEATURE
<222> LOCATION: (71)..(71)
```

<223> OTHER INFORMATION: X= H or R
<220> FEATURE:
<221> NAME/KEY: MISC_FEATURE
<222> LOCATION: (72)..(72)
<223> OTHER INFORMATION: X= Q or H
<220> FEATURE:
<221> NAME/KEY: MISC_FEATURE
<222> LOCATION: (73)..(73)
<223> OTHER INFORMATION: X= R, S or K
<220> FEATURE:
<221> NAME/KEY: MISC_FEATURE
<222> LOCATION: (75)..(75)
<223> OTHER INFORMATION: X= A, V or P
<220> FEATURE:
<221> NAME/KEY: MISC_FEATURE
<222> LOCATION: (76)..(76)
<223> OTHER INFORMATION: X= P or S
<220> FEATURE:
<221> NAME/KEY: MISC_FEATURE
<222> LOCATION: (77)..(77)
<223> OTHER INFORMATION: X= P or T

<400> SEQUENCE: 10

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
    50                  55                  60

Arg Asp Pro Xaa Leu Xaa Xaa Xaa Xaa Pro Xaa Xaa Xaa
65                  70                  75

<210> SEQ ID NO 11
<211> LENGTH: 77
<212> TYPE: PRT
<213> ORGANISM: Artificial Sequence
<220> FEATURE:
<223> OTHER INFORMATION: primate sushi and domains consensus sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:

```
<221> NAME/KEY: MISC_FEATURE
<222> LOCATION: (68)..(68)
<223> OTHER INFORMATION: X= A, S or L
<220> FEATURE:
<221> NAME/KEY: MISC_FEATURE
<222> LOCATION: (70)..(70)
<223> OTHER INFORMATION: X= V, A or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (75)..(75)
<223> OTHER INFORMATION: X= A or V

<400> SEQUENCE: 11

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys Ile
    50                  55                  60

Arg Asp Pro Xaa Leu Xaa Xaa Gln Arg Pro Xaa Pro Pro
65                  70                  75

<210> SEQ ID NO 12
<211> LENGTH: 77
<212> TYPE: PRT
<213> ORGANISM: Homo sapiens

<400> SEQUENCE: 12

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro
65                  70                  75

<210> SEQ ID NO 13
<211> LENGTH: 20
<212> TYPE: PRT
<213> ORGANISM: Artificial Sequence
<220> FEATURE:
<223> OTHER INFORMATION: peptidic linker

<400> SEQUENCE: 13

Ser Gly Gly Ser Gly Gly Gly Ser Gly Gly Ser Gly Gly
1               5                   10                  15

Gly Ser Leu Gln
            20

<210> SEQ ID NO 14
<211> LENGTH: 20
<212> TYPE: PRT
<213> ORGANISM: Artificial Sequence
<220> FEATURE:
<223> OTHER INFORMATION: peptidic linker
```

-continued

```
<400> SEQUENCE: 14

Ser Gly Gly Ser Gly Gly Gly Ser Gly Gly Ser Gly Gly
1               5                   10                  15

Gly Ser Gly Gly
            20

<210> SEQ ID NO 15
<211> LENGTH: 21
<212> TYPE: PRT
<213> ORGANISM: Artificial Sequence
<220> FEATURE:
<223> OTHER INFORMATION: peptidic linker

<400> SEQUENCE: 15

Ser Gly Gly Gly Ser Gly Gly Gly Ser Gly Gly Gly Ser Gly
1               5                   10                  15

Gly Gly Ser Leu Gln
            20

<210> SEQ ID NO 16
<211> LENGTH: 18
<212> TYPE: PRT
<213> ORGANISM: Artificial Sequence
<220> FEATURE:
<223> OTHER INFORMATION: peptidic linker

<400> SEQUENCE: 16

Ser Gly Gly Ser Gly Gly Gly Ser Gly Gly Ser Gly Gly Gly
1               5                   10                  15

Gly Ser

<210> SEQ ID NO 17
<211> LENGTH: 211
<212> TYPE: PRT
<213> ORGANISM: Artificial Sequence
<220> FEATURE:
<223> OTHER INFORMATION: RLI

<400> SEQUENCE: 17

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Ser Gly Gly Gly Ser Gly Gly Gly Gly Ser Gly
                85                  90                  95

Gly Asn Trp Val Asn Val Ile Ser Asp Leu Lys Lys Ile Glu Asp Leu
                100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
        130                 135                 140

Gln Val Ile Ser Leu Glu Ser Gly Asp Ala Ser Ile His Asp Thr Val
145                 150                 155                 160
```

```
Glu Asn Leu Ile Ile Leu Ala Asn Asn Ser Leu Ser Ser Asn Gly Asn
            165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
            195                 200                 205

Asn Thr Ser
    210

<210> SEQ ID NO 18
<211> LENGTH: 211
<212> TYPE: PRT
<213> ORGANISM: Artificial Sequence
<220> FEATURE:
<223> OTHER INFORMATION: ANti-HER2Neu light chain

<400> SEQUENCE: 18

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Gly Ser Leu
            85                  90                  95

Gln Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
            130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
            165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
            195                 200                 205

Asn Thr Ser
    210
```

CYTOKINE DERIVED TREATMENT WITH REDUCED VASCULAR LEAK SYNDROME

This International patent application claims the priority of the European patent application EP 13002066.2 filed on Apr. 19, 2013, which is herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480275_402USPC_SEQUENCE_LISTING.txt. The text file is 25.7 KB, was created on Oct. 11, 2015, and is being submitted electronically via EFS-Web.

FIELD OF THE INVENTION

The present invention relates to a new pharmaceutical composition and associated method for treating cancer and/or infection in a subject.

BACKGROUND

Immunotherapies has developed in the last decades so as overcome the inability of the immune system to efficiently protect against the establishment of tumors or microbes, or reject established tumors or microbes.

Among immunotherapies, those based on cytokines are of particular interest. These molecules, which are soluble molecules, are regulating the humoral and/or cellular immunity. Among them, IL-2, IL-7, IL-12 and IL-15 are of more particular interest since they are inducing NK cells survival and/or proliferation; thus being interesting as adjuvant for treating infection or cancer.

As an example, Human rIL-2 has been shown to result in tumor regression in 25-30% of patients with metastatic melanoma or renal carcinoma. As Intermittent IL-2 therapy is also used in HIV-infected patients in combination with highly active antiretroviral therapy and restores sustained, protective levels of CD4+ T lymphocytes.

Nevertheless, the use of such cytokines is restricted because of their dose-dependent toxicity, which manifests particularly as vascular leak syndrome (VLS), which is characterized by increased vascular permeability and decreased microcirculatory perfusion, leading to interstitial edema and multiple organ failure within 2-24 h of IL-2 administration.

The analysis of the mechanism of cytokine-induced VLS has demonstrated the implication of cytokine induced-NK cells in some phases of VLS (ASSIER et al., *Cytokines*, vol. 32(6), p: 280-6, 2005). The VLS implication of T cells has also been established since VLS is accentuated by depletion of Treg cells (KOTTKE et al., *Mol. Ther.*, vol. 16(7), p: 1217-26, 2008).

Finally, the use of cytokines is actually limited to a maximum NK cells proliferation induction, so as not to induce unacceptable or lethal VLS.

Because of this requirement and problematic safety, the use of high dose of cytokines is actually limited to chronic infections and to advanced metastatic cancer.

SUMMARY OF THE INVENTION

Now, the inventors have surprisingly established that their molecule (RLI) comprising the hIL-15 amino acids sequence shows a very different safety as compared to the one of IL-15 or IL-2, which RLI safety is much more favorable. Finally, their results established that RLI can be used in a therapeutic window, which is unthinkable for both IL-2 and IL-15.

This safety enables the use of high dose of RLI for treating diseases associated with bad prognosis and lowest dose of RLI for treating diseases associated with correct or good prognosis.

Thus, the invention relates in a first aspect, to a composition for treating a cancer, an infection or an immunodeficiency disorder in a subject by administrating to said subject an amount of a conjugate so as to induce a proliferation of natural killer cells (NK cells) which is the same or higher than the one obtained with high dose of interleukin-2 (HDIL-2), wherein said conjugate comprises:
a) a polypeptide comprising the amino acid sequence of interleukin 15 or derivatives thereof, and
b) a polypeptide comprising the amino acid sequence of the sushi domain of IL-15Rα or derivatives thereof.

In a second aspect, the present invention relates to a method for treating a cancer, an infection or an immunodeficiency disorder in a subject comprising the step of administrating to a subject in need thereof an amount of a conjugate so as to induce a proliferation of natural killer cells (NK cells) which is the same or higher than the one obtained with HDIL-2, wherein said conjugate comprises:
a) a polypeptide comprising the amino acid sequence of interleukin 15 or derivatives thereof, and
b) a polypeptide comprising the amino acid sequence of the sushi domain of IL-15Rα or derivatives thereof.

Preferably, the conjugate is also administrated in an amount inducing a proliferation of CD8 T cells higher than the one obtained with HDIL-2.

In a third preferred embodiment, said conjugate is administrated to the subject in an amount inducing a proliferation of Treg cells (FoxP3+CD4+CD25$^{high}$) which is less to the one obtained with HDIL-2.

In a third aspect, the present invention relates to a (in vitro) method for determining the therapeutically efficient amount of conjugate to be administrated to a subject suffering from a cancer, from an infection or from an immunodeficient disorder, said method comprising the step of:
i) contacting peripheral blood mononucleated cells (PBMCs) from said subject with increasing amounts of the conjugate defined previously in culture conditions enabling the proliferation of said PBMCs;
ii) contacting other PBMCs from said subject with High Dose of interleukin-2 (HDIL-2) in culture conditions enabling the proliferation of said PBMCs; and
iv) selecting a therapeutically efficient amount of conjugate, said therapeutically efficient amount inducing a proliferation of NK cells of said PBMCs which is the same or higher than the one obtained with HDIL-2.

Still preferably, said amount of conjugate induces a ratio of the percentage of proliferating NK cells and/or of CD8 T cells on the one of Treg cells which is at least 25% higher than the one obtained with HDIL-2; preferably at least 50% higher; and still preferably at least 75% higher than the one obtained with HDIL-2.

Figure 13:
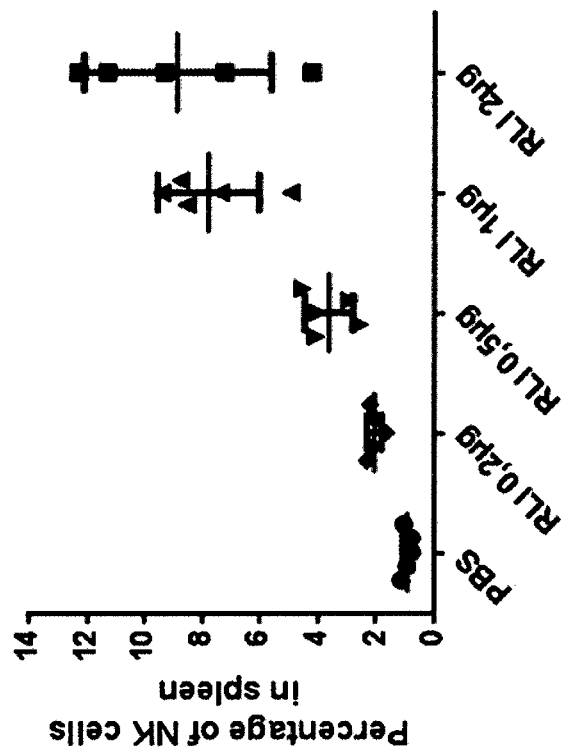
Figure 13:
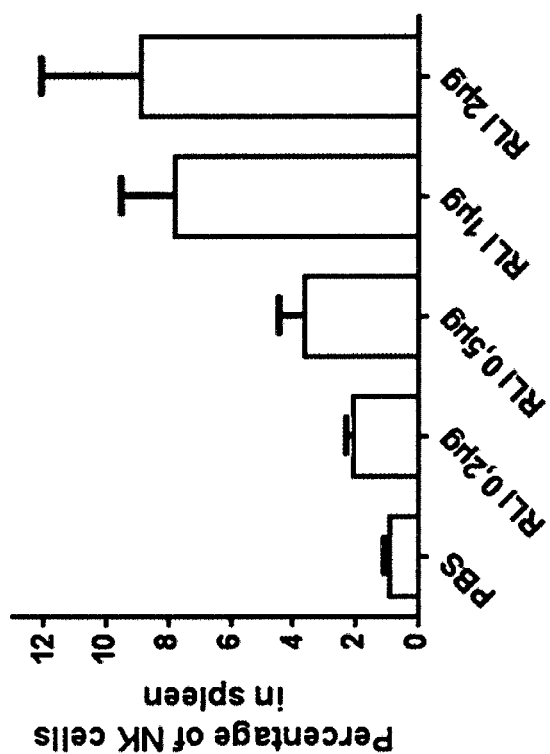

The FIG. 13 represents the dose-response effect of RLI on NK cell expansion.

Figure 14:
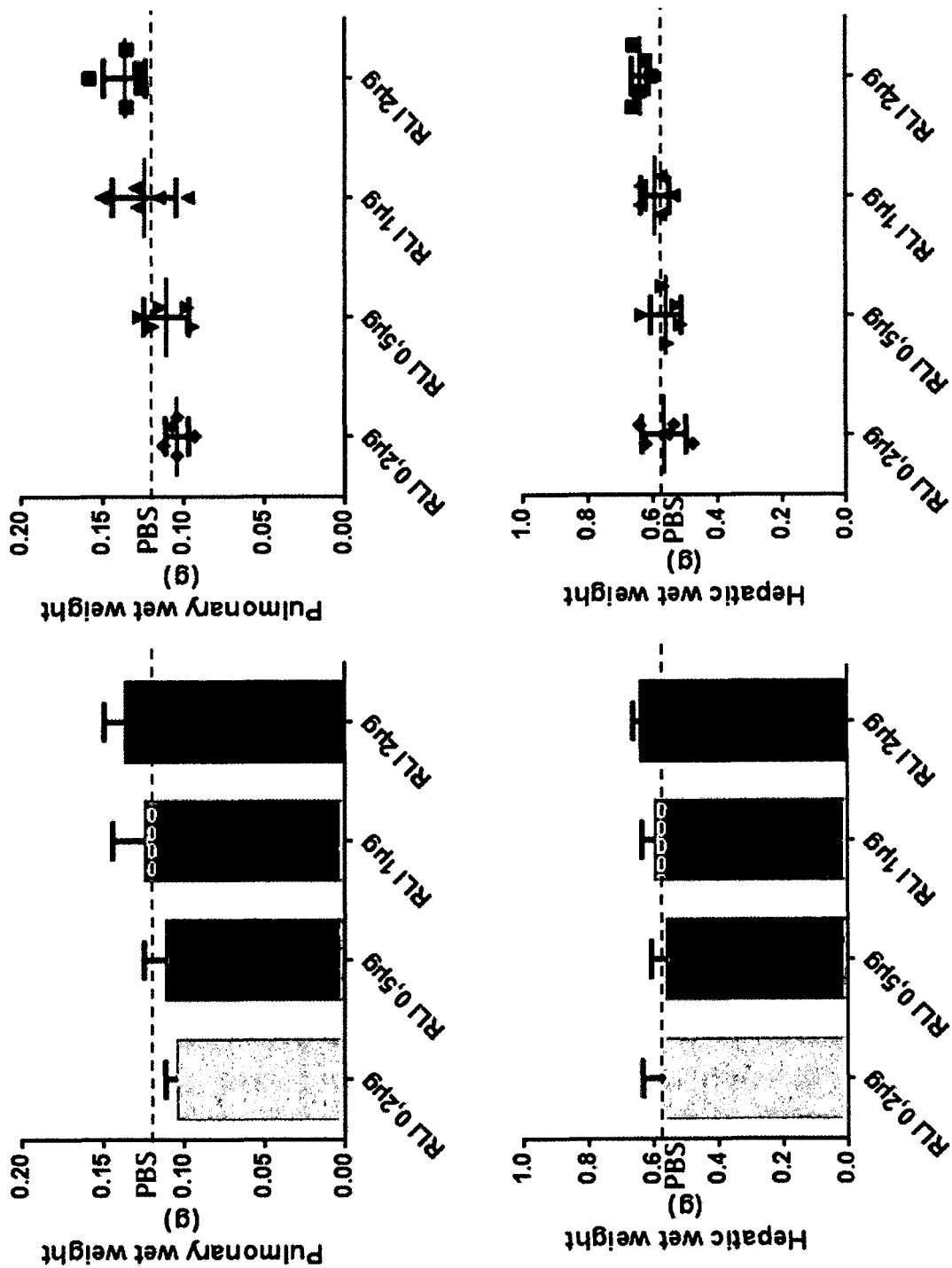

FIG. 14 represents the dose-response effect of RLI on VLS in lung and liver.

Figure 15:
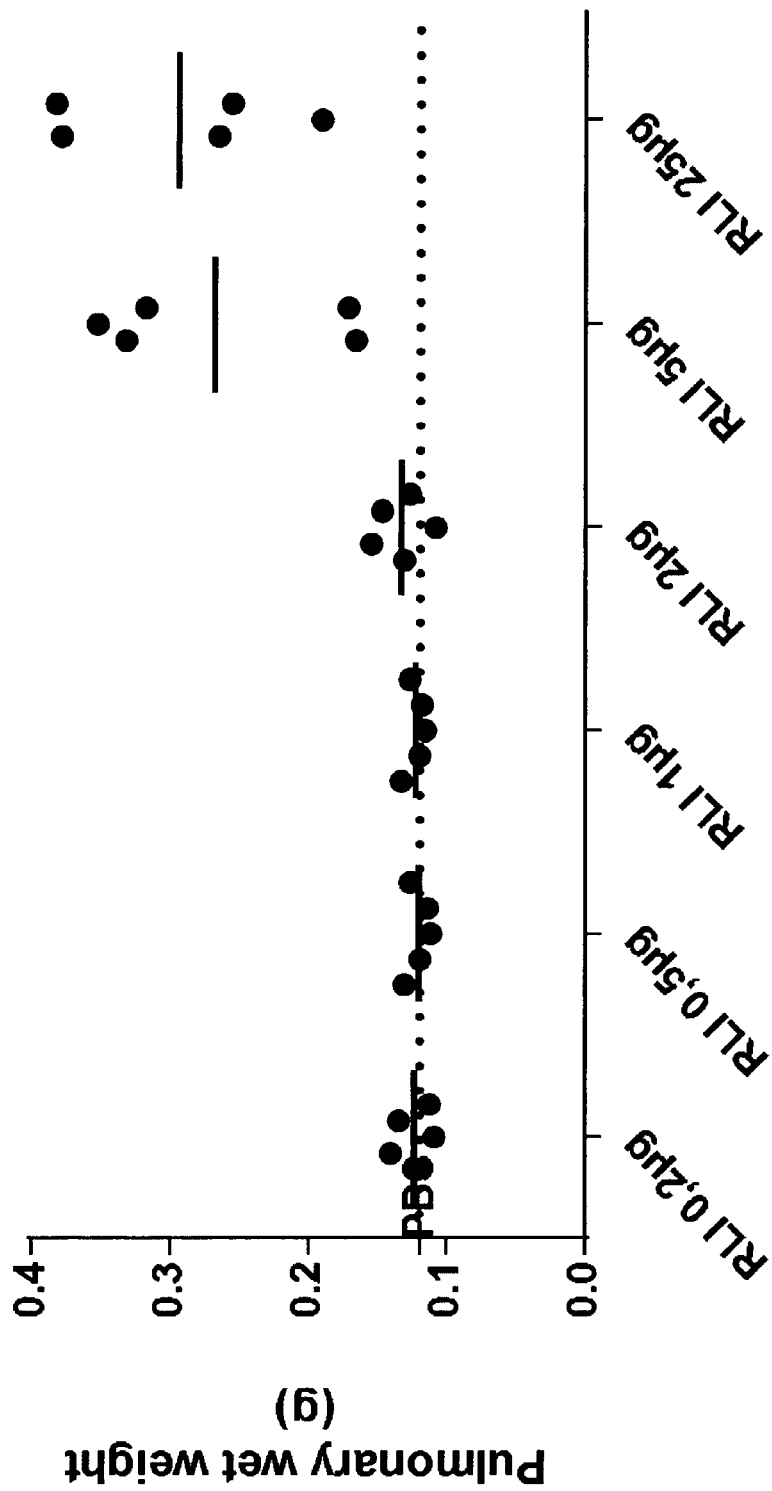

FIG. 15 represents the dose-response effect of RLI on VLS in lung.

Figure 16:
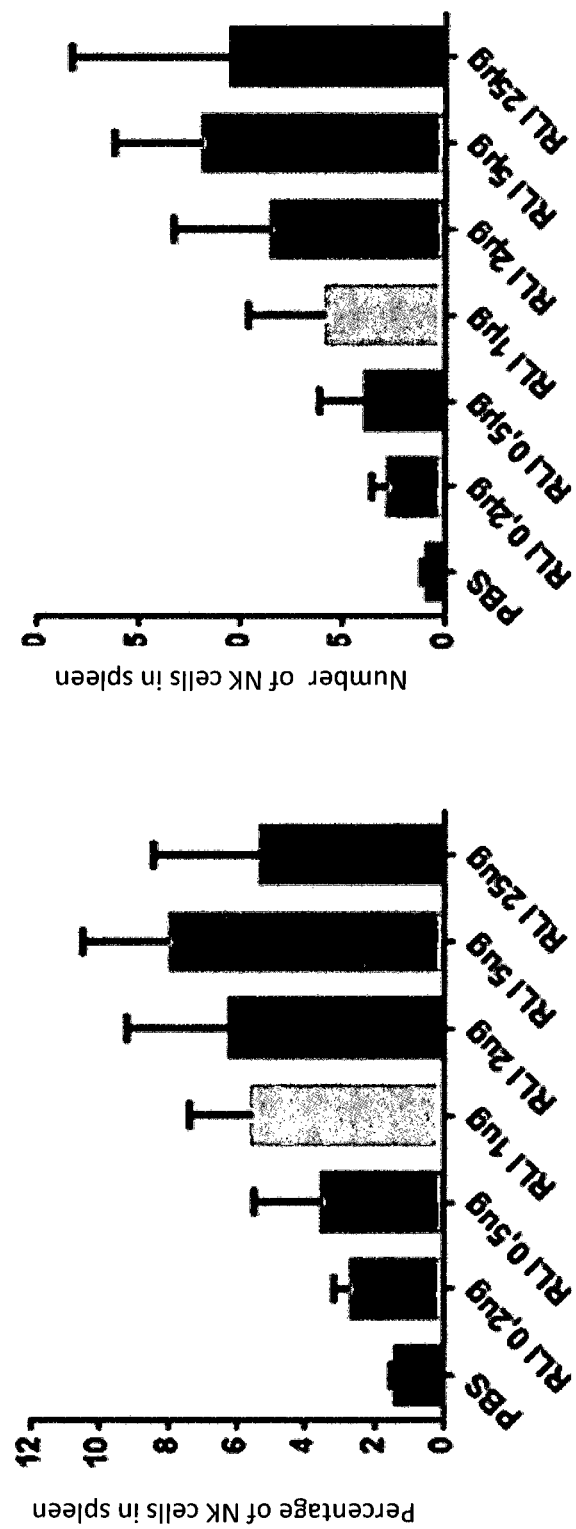

FIG. 16 represents the dose-response effect of RLI on NK cell expansion.

Figure 17:
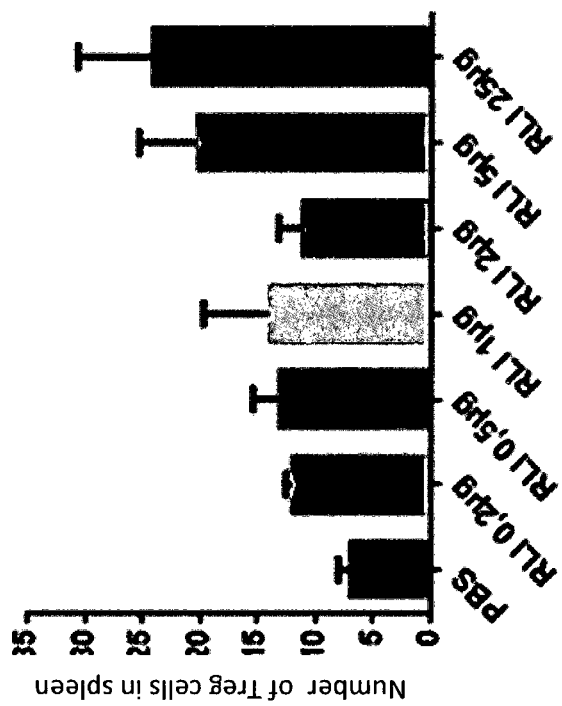
Figure 17:
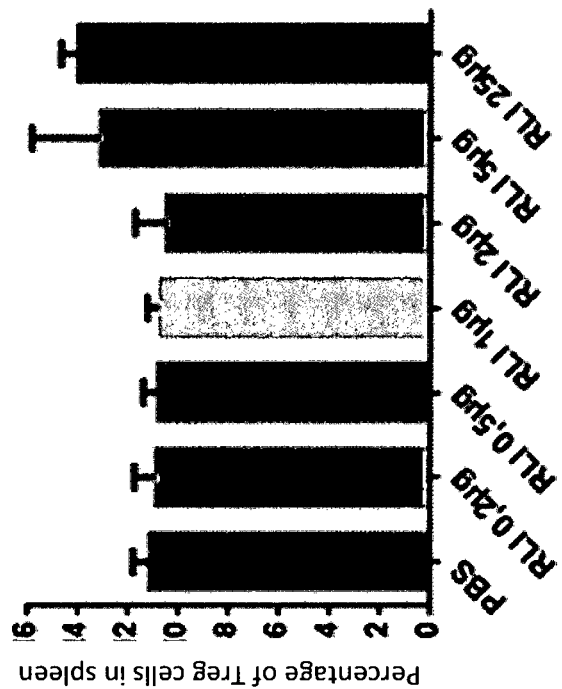

FIG. 17 represents the dose-response effect of RLI on Treg cell expansion.

Figure 18:
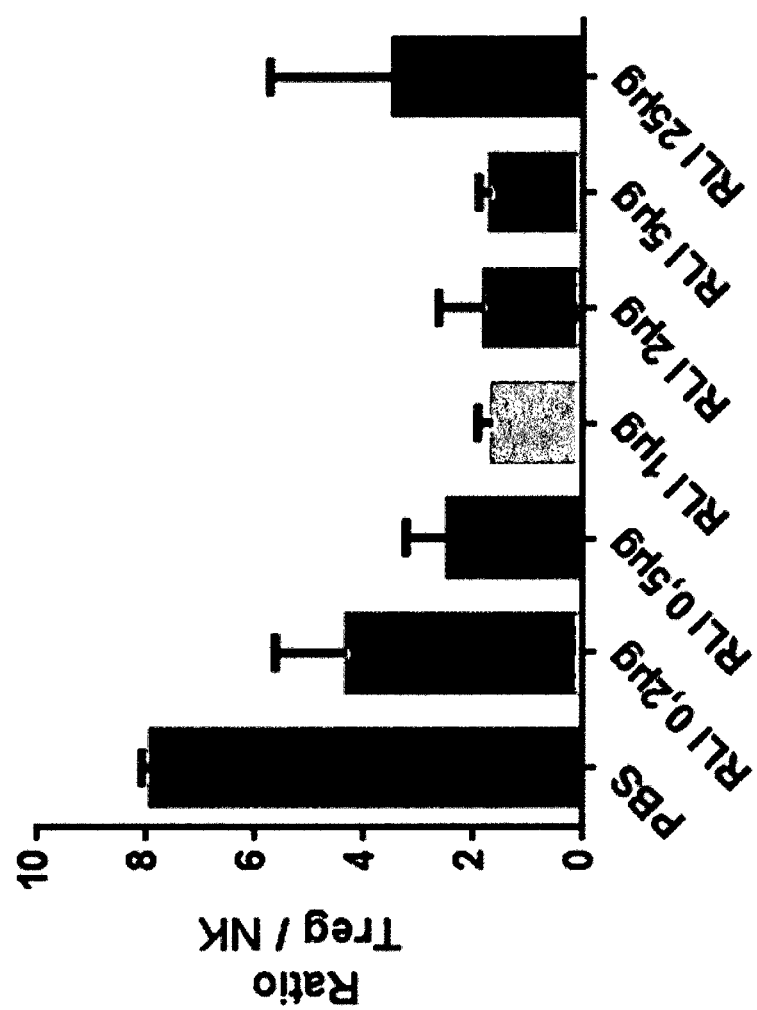

FIG. 18 represents the dose-response effect of RLI on the ratio of percentage Treg versus NK cells.

Figure 19:
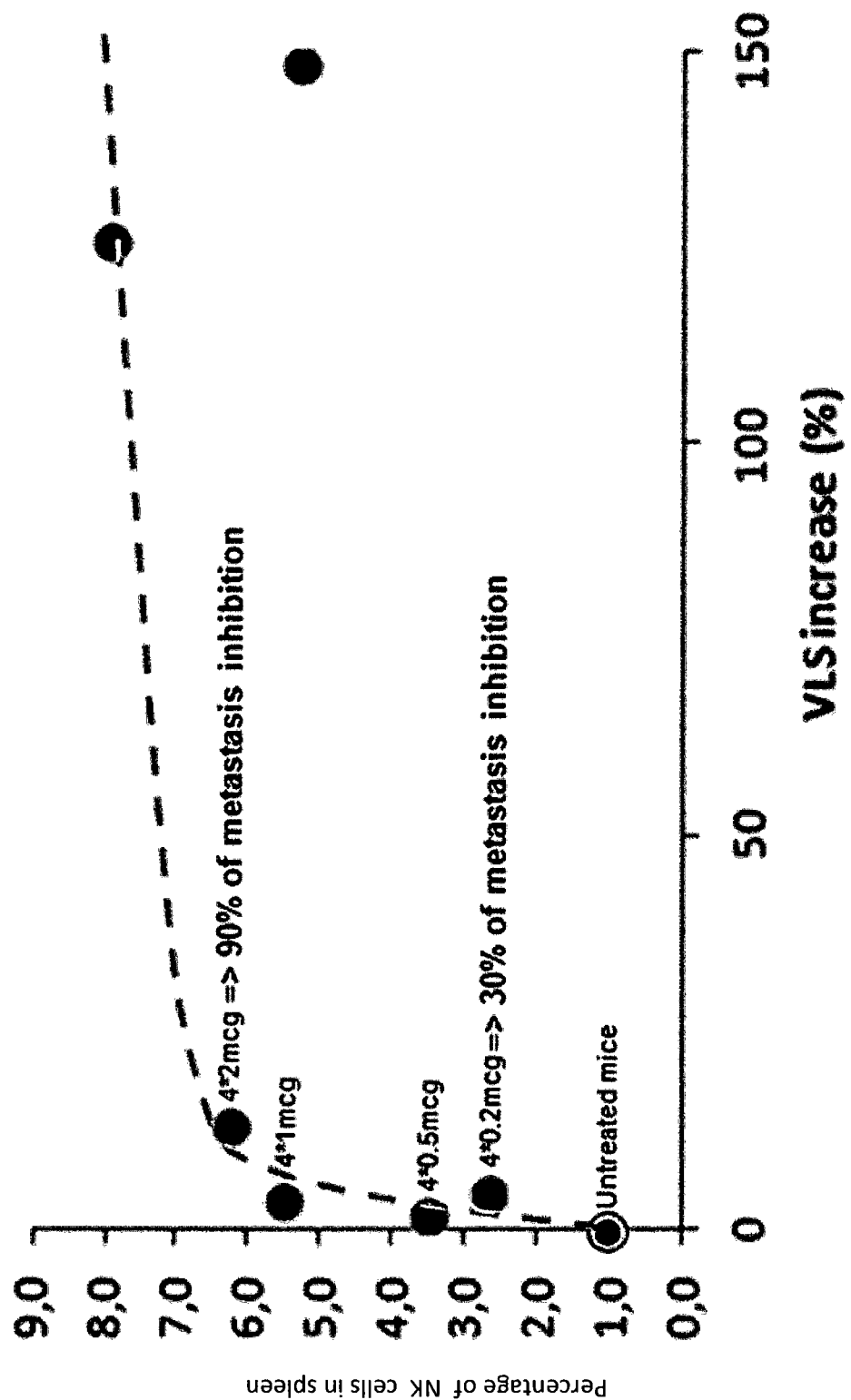

FIG. 19 represents the pharmacological efficacy versus toxicity for RLI.

DETAILED DESCRIPTION

As used herein, the term "subject" denotes a mammal, such as a rodent, a feline, a canine or a primate, and most preferably a human.

The term "conjugate" in its general meaning in the art and refers to a covalent or non covalent complex, preferably to a covalent complex and most preferably to a fusion protein.

The term "interleukin 2" is used in its general meaning in the art (for the nucleic acid and amino acid sequences, see accession numbers NM_000586.3 and NP_000577.2 respectively).

The expression "high dose of interleukin-2" or "HDIL-2" is well known from the skilled person. High dose of IL-2 (600,000-720,000 IU/kg by IV every 8 h) is the most commonly used regimen in the United States. As an example, the Food and Drug Administration (FDA)-approved dosage for treatment of metastatic renal cell carcinoma or melanoma (cancer with median prognosis of less than 6 months) is 600,000 IU/kg administered by IV bolus over 15 minutes every 8 hours for a maximum of 14 doses. Following 9 days of rest, the regimen is repeated, if tolerated by the patient. Low-dose subcutaneous IL-2 regimens (1-30 million IU/m²/d) have been investigated because they may reduce toxicity but compromise efficacy (FYFE, FISHER & ROSENBERG et al., *J. Clin. Oncol.*, vol. 13, p: 668-696, 1995). PROLEUKIN® biological potency is determined by a lymphocyte proliferation bioassay and is expressed in International Units as established by the World Health Organization 1st International Standard for Interleukin-2 (human). The relationship between potency and protein mass is as follows: 18 million International Units PROLEUKIN=1.1 mg protein.

It should be noticed that the legal authorities (e.g. FDA, EMA, etc.) tolerate much more side effects for treatments of lethal diseases (e.g. metastatic renal cell carcinoma or melanoma) increasing patient survival in the absence of alternative treatments.

The term "interleukin 15" in its general meaning in the art and refers to a cytokine with structural similarity to IL-2 (GRABSTEIN et al., *Science*, vol. 264(5161), p: 965-968, 1994). This cytokine is also known as IL-15, IL15 or MGC9721. This cytokine and IL-2 share many biological activities and they were found to bind common hematopoietin receptor subunits. Thus, they may compete for the same receptor, negatively regulating each other's activity. It has been established that IL-15 regulates T and natural killer cells activation and proliferation, and that the number of CD8+ memory cells is shown to be controlled by a balance between this cytokine and IL2. IL-15 activity can be measured by determining its proliferation induction on kit225 cell line (HORI et al., *Blood*, vol. 70(4), p: 1069-72, 1987), as disclosed in the Examples.

Said IL-15 or derivatives thereof have at least 10% of the activity of human interleukin-15 on the proliferation induction of kit225 cell line, preferably at least 25% and more preferably at least 50%.

Said interleukin 15 is a mammalian interleukin 15, preferably a primate interleukin 15, and more preferably a human interleukin 15.

Mammalian interleukin 15 can be simply identified by the skilled person. As an example, one can cite Interleukin 15 from *Sus scrofa* (Accession number ABF82250), from *Rattus norvegicus* (Accession number NP_037261), from *Mus musculus* (Accession number NP_032383), from *Bos Taurus* (Accession number NP_776515), from *Oryctolagus cuniculus* (Accession number NP_001075685), from *Ovies aries* (Accession number NP_001009734), from *Felis catus* (Accession number NP_001009207), from *Macaca fascicularis* (Accession number BAA19149), from *Homo sapiens* (Accession number NP_000576), from *Macaca Mulatta* (Accession number NP_001038196), from *Cavia porcellus* (Accession number NP_001166300), or from *Chlorocebus sabaeus* (Accession number ACI289).

As used herein, the term "mammalian interleukin 15" refers to the consensus sequence SEQ ID no 1.

Primate interleukin 15 can be simply identified by the skilled person. As an example, one can cite Interleukin 15 from *Sus scrofa* (Accession number ABF82250), from *Oryctolagus cuniculus* (Accession number NP_001075685), from *Macaca fascicularis* (Accession number BAA19149), from *Homo sapiens* (Accession number NP_000576), from *Macaca Mulatta* (Accession number NP_001038196), or from *Chlorocebus sabaeus* (Accession number ACI289).

As used herein, the term "primate interleukin 15" refers to the consensus sequence SEQ ID no 2.

Human interleukin 15 can be simply identify by the skilled person and refers to the amino acids sequence SEQ ID no 3.

As used herein, the term "interleukin 15 derivatives" refers to an amino acid sequence having a percentage of identity of at least 92.5% (i.e. corresponding to about 10 amino acids substitutions) with an amino acid sequence selected in the group consisting of SEQ ID no: 1, SEQ ID no 2 and SEQ ID no 3, preferably of at least 96% (i.e. corresponding to about 5 amino acids substitutions), and more preferably of at least 98.5% (i.e. corresponding to about 2 amino acids substitutions) or of at least 99% i.e. corresponding to about 1 amino acid substitution). Such derivatives can be simply identified by the skilled person in view of its personal knowledge and of the teaching of the present patent application. As an example of such derivatives, one can cite those described in the International Patent Application PCT WO 2009/135031. It will also be understood that natural amino acids may be replaced by chemically modified amino acids. Typically, such chemically modified amino acids increase the polypeptide half life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the local homology algorithm developed by SMITH and WATERMAN (*Ad. App. Math.*, vol. 2, p: 482, 1981), by using the global homology algorithm developed by NEDDLEMAN and WUNSCH (*J. Mol. Biol.*, vol. 48, p: 443, 1970), by using the method of similarities developed by PEARSON and LIPMOLAN (*Proc. Natl. Acad. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Preferably, the interleukin 15 derivatives are IL-15 agonist or superagonist. One skilled in the art can simply identify an IL-15-agonist or -superagonist. As a example of IL-15-agonist or -superagonist, one can cite the ones disclosed in the International patent application WO 2005/085282 or in ZHU et al. (*J. Immunol.*, vol. 183(6), p: 3598-607, 2009).

Still preferably, said IL-15 agonist or superagonist is selected in the group comprising/consisting of L45D, L45E, S51D, L52D, N72D, N72E, N72A, N72S, N72Y and N72P (in reference to sequence of human IL-15, SEQ ID no 3).

As used herein the term "the sushi domain of IL-15Rα" has its general meaning in the art and refers to a domain beginning at the first cysteine residue (C1) after the signal peptide of IL-15Rα, and ending at the fourth cysteine residue (C4) after said signal peptide. Said sushi domain corresponding to a portion of the extracellular region of IL-15Rα is necessary for its binding to IL-15 (WEI et al., *J. Immunol.*, vol. 167(1), p: 277-282, 2001).

Said sushi domain of IL-15Rα or derivatives thereof has at least 10% of the binding activity of the sushi domain of human IL-15Rα to human interleukin-15, preferably at least 25% and more preferably at least 50%. Said binding activity can be simply determined by the method disclosed in WEI et al. (abovementioned, 2001).

Said sushi domain of the IL-15Rα is the sushi domain of a mammalian IL-15Rα, preferably the sushi domain of a primate IL-15Rα and more preferably the sushi domain of the human IL-15Rα.

The sushi domain of a mammalian IL-15Rα can be simply identified by the skilled person. As an example, one can cite the sushi domain of a IL-15Rα from *Rattus norvegicus* (Accession number XP_002728555), from *Mus musculus* (Accession number EDL08026), from *Bos Taurus* (Accession number XP_002692113), from *Oryctolagus cuniculus* (Accession number XP_002723298), from *Macaca fascicularis* (Accession number ACI42785), from *Macaca nemestrina* (Accession number ACI42783), from *Homo sapiens* (Accession number CAI41081), from *Macaca Mulatta* (Accession number NP 001166315), *Pongo abelii* (Accession number XP_002820541), *Cercocebus torquatus* (Accession number ACI42784), *Callithrix jacchus* (Accession number XP_002750073), or from *Cavia porcellus* (Accession number NP_001166314).

As used herein, the term "sushi domain of a mammalian IL-15Rα" refers to the consensus sequence SEQ ID no 4.

Preferably, the polypeptide comprising the amino acid sequence of the sushi domain of a mammalian IL-15Rα refers to the consensus sequence SEQ ID no 5.

The sushi domain of a primate IL-15Rα can be simply identified by the skilled person. As an example, one can cite sushi domains of IL-15Rα from *Oryctolagus cuniculus*, from *Macaca fascicularis*, from *Macaca nemestrina*, from *Homo sapiens*, from *Macaca Mulatta*, *Pongo abelii*, *Cercocebus torquatus*, or *Callithrix jacchus*.

As used herein, the term "sushi domain of a primate IL-15Rα" refers to the consensus sequence SEQ ID no 6.

Preferably, the polypeptide comprising the amino acid sequence of the sushi domain of a primate IL-15Rα refers to the consensus sequence SEQ ID no 7.

The sushi domain of human IL-15Rα can be simply identified by the skilled person and refers to the amino acids sequence SEQ ID no 8.

Preferably, the polypeptide comprising the amino acid sequence of the sushi domain of human IL-15Rα refers to SEQ ID no 9.

As used herein, the term "derivatives of the sushi domain of the IL-15Rα" refers to an amino acid sequence having a percentage of identity of at least 92% (i.e. corresponding to about 5 amino acids substitutions) with an amino acid sequence selected in the group consisting of SEQ ID no: 4, SEQ ID no 5, SEQ ID no 6, SEQ ID no: 7, SEQ ID no 8, and SEQ ID no 9, preferably of at least 96% (i.e. corresponding to about 2 amino acids substitutions), and more preferably of at least 98% (i.e. corresponding to about 1 amino acids substitutions). Such derivatives comprise the four cysteine residues of the sushi domain of L-15Rα and can be simply identified by the skilled person in view of his/her general knowledge and of the teaching of the present patent application. It will also be understood that natural amino acids may be replaced by chemically modified amino acids. Typically, such chemically modified amino acids enable to increase the polypeptide half life.

According to a preferred embodiment, the conjugate comprises (ii) a polypeptide comprising the amino acid sequence of the sushi and hinge domains of IL-15Rα or derivatives thereof.

The IL-15Rα hinge domain is defined as the amino acid sequence that begins at the first amino residue after the sushi domain and that ends at the last amino acid residue before the first potential site of glycosylation. In human IL-15Rα, the amino acid sequence of the hinge region consists of the fourteen amino acids which are located after the sushi domain of this IL-15Ralpha, in a C-terminal position relative to said sushi domain, i.e., said IL-15Ralpha hinge region begins at the first amino acid after said (C4) cysteine residue, and ends at the fourteenth amino acid (counting in the standard "from N-terminal to C-terminal" orientation).

Said sushi and hinge domains of IL-15Rα are the sushi and hinge domains of a mammalian IL-15Rα, preferably the sushi and hinge domains of a primate IL-15Rα and more preferably the sushi and hinge domains of the human IL-15Rα.

The amino acid sequence of the sushi and hinge domains of a mammalian IL-15Rα can be simply identified by the skilled person. As used herein, the term "sushi and hinge domains of a mammalian IL-15Rα" refers to the consensus sequence SEQ ID no 10.

The amino acid sequence of the sushi and hinge domains of a primate IL-15Rα can be simply identified by the skilled person. As used herein, the term "sushi and hinge domains of a primate IL-15Rα" refers to the consensus sequence SEQ ID no 11.

The amino acid sequence of the sushi and hinge domains of human IL-15Rα can be simply identified by the skilled person. As used herein, the term "sushi and hinge domains of human IL-15Rα" refers to the consensus sequence SEQ ID no 12.

As used herein, the term "derivatives of the sushi and hinge domains of IL-15Rα" refers to an amino acid sequence having a percentage of identity of at least 93% (i.e. corresponding to about 5 amino acids substitutions) with an amino acid sequence selected in the group consisting of SEQ ID no: 10, SEQ ID no 11, and SEQ ID no 12, preferably of at least 97% (i.e. corresponding to about 2 amino acids substitutions), and more preferably of at least 98% (i.e. corresponding to about 1 amino acids substitution). Such derivatives comprise the four cysteine residues of the sushi domain of L-15Rα and can be simply identified by the skilled person in view of its general knowledge and of the teaching of the present patent application. It will also be understood that natural amino acids may be replaced by chemically modified amino acids. Typically, such chemically modified amino acids enable to increase the polypeptide half-life.

Both polypeptides a) and b) of the conjugate may be linked non-covalently such as in the complex disclosed in U.S. Pat. No. 8,124,084 B2 and in the International patent application WO 2012/040323. Said conjugate or complex can be simply obtained by providing a suitable amount of the polypeptide a), providing a suitable amount of the polypeptide b), admixing both polypeptides under suitable pH and ionic conditions for a duration sufficient to allow complex (i.e. conjugate) formation, and optionally concentrating or purifying said complex. The polypeptides of the complex (i.e. conjugate) can be formed, for example, using a peptide synthesizer according to standard methods; by expressing each polypeptide separately in a cell or cell extract, then isolating and purifying the polypeptide. Optionally, the therapeutic polypeptide complex of the invention can be formed by expressing both polypeptides i) and ii) in the same cell or cell extract, then isolating and purifying the complexes, for example, using chromatographic techniques, such as affinity chromatography with antibodies to the lymphokine portion, the lymphokine receptor portion, or to the complex.

Both polypeptides a) and b) of the conjugate may be also covalently linked using bifunctional protein coupling agents or in a fusion protein.

Bifunctional protein coupling agents are well known from the skilled person such as methods using them, and include, as examples, N-succinimidyl(2-pyridyldithio) propionate (SPDP), succinimidyl(N-maleimidomethyl)cyclohexane-1-carboxylate, iminothiolane (IT), bifunctional derivatives of imidoesters (such as dimethyl adipimidateHCL), active esters (such as disuccinimidylsuberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene).

The term "fusion protein" refers to a protein created through the joining of two or more genes which originally coded for separate proteins. It is also known as a chimeric protein. Translation of this fusion gene results in a single polypeptide with functional properties deriving from each of the original proteins. Recombinant fusion proteins are created artificially by recombinant DNA technology for use in biological research or therapeutics. A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

In a preferred embodiment, the conjugate is a fusion protein.

The amino acid sequence of interleukin 15 or derivatives thereof can be in a C-terminal or in an N-terminal position relative to the amino acid sequence of the sushi domain of IL-15Rα or derivatives thereof. Preferably, the amino acid sequence of the interleukin 15 or derivatives thereof is in a C-terminal position relative to the amino acid sequence of the sushi domain of IL-15Rα or derivatives thereof.

The amino acid sequence of interleukin 15 or derivatives thereof and the amino acid sequence of the sushi domain of IL-15Rα or derivatives thereof may be separated by a "linker" amino acid sequence. Said "linker" amino acid sequence may be of a length sufficient to ensure that the fusion protein form proper secondary and tertiary structures.

The length of the linker amino acid sequence may vary without significantly affecting the biological activity of the fusion protein. Typically, the linker amino acid sequence comprises at least one, but less than 30 amino acids e.g., a linker of 5-30 amino acids, preferably of 10-30 amino acids, more preferably of 15-30 amino acids, still more preferably of 15-25 amino acids, most preferably of 18-22 amino acids.

Preferred linker amino acid sequences are those which allow the conjugate to adopt a proper conformation (i.e., a conformation allowing a proper signal transducing activity through the IL-15Rbeta/gamma signaling pathway).

The most suitable linker amino acid sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains.

Preferably, the linker amino acid sequence comprises near neutral amino acids selected in the group comprising Gly (G), Asn (N), Ser (S), Thr (T), Ala (A), Leu (L), and Gln (Q), most preferably in the group comprising Gly (G), Asn (N), and Ser (S).

Examples of linker sequences are described in U.S. Pat. Nos. 5,073,627 and 5,108,910.

Illustrative flexible linkers that are more particularly suitable for the present invention include those coded by the sequences of SEQ ID no 13 (SGGSGGGGSGGGSGGGGSLQ), SEQ ID no 14 (SGGSGGGGSGGGSGGGGSGG) or SEQ ID no 15 (SGGGSGGGGSGGGGSGGGSLQ), and SEQ ID no 16 (SGGSGGGGSGGGSGGGS).

In a still preferred embodiment, the conjugate corresponds to a fusion protein with the sequence SEQ ID no 17 or SEQ ID no 18.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

The route of administration of the combination of the invention is preferably parenteral; as used herein, the term "parenteral" includes intravenous, intramuscular, subcutaneous, rectal, vaginal or intraperitoneal administration. Thus, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

Of these, intravenous administration is most preferred.

The conjugate may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly(lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Dispersions can also be prepared in glycerol, liquid polyethylene glycols, and mixtures thereof and in oils. Under ordinary conditions of storage and use, these preparations contain a preservative to prevent the growth of microorganisms.

The conjugate can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The conjugates of the invention may also be modified, by pegylation as an example, so as to increase its biodisponibility.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, half-life enhancing covalent and non covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In the context of the invention, the term "treating", as used herein, means reversing, alleviating, inhibiting the progress of, or preventing the disorder or condition to which such term applies, or one or more symptoms of such disorder or condition.

The term "treating cancer" as used herein means the inhibition of the growth of cancer cells. Preferably such treatment also leads to the regression of tumor growth, i.e., the decrease in size of a measurable tumor. Most preferably, such treatment leads to the complete regression of the tumor.

The term "treating an infection" as used herein means the inhibition of microbes replication/proliferation.

The term "treating an immunodeficiency disorder" as used herein means the induction of NK cells and/or T cells.

An "effective amount" of the conjugate is an amount which is sufficient to induce the regression of tumor growth or of microbes' replication. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

Because of the very important safety of the conjugate of the invention, its administration can be envisaged for treating cancer, infection and immunodeficiency disorder with a very important therapeutic window, far from the restricted IL-2 therapeutic window and also from the therapeutic window envisaged for IL-15.

This safety enable to envisage the use of 1) very high dose of RLI for treating chronic disease with bad prognosis (e.g. metastatic renal adenocarnima or melanoma) and 2) low dose of RLI for treating disease with good prognosis.

The administered amount also induces a proliferation of CD8 T cells that is higher than the one obtained with HDIL-2.

As an illustration, an effective amount of the at least one conjugate is higher than 40 fmol/kg or 0.2 pmol/kg (1 ng/kg or 5 ng/kg), preferably greater than 1 pmol/kg or 2 pmol/kg (25 ng/kg or 50 ng/kg), and still preferably greater than 4 pmol/kg (100 ng/kg), 20 pmol/kg (500 ng/kg), or even greater than 40 pmol/kg (1 mcg/kg). Other dosages are viable, since the molecular weight and the activity of the conjugate thereof may influence it. The skilled artisan is readily credited with determining a suitable dosage that falls within the ranges, or if necessary, outside of the ranges.

As another illustration, an effective amount of the at least one conjugate corresponds to a blood concentration higher than 4 fmol/ml (0.1 ng/ml), preferably higher than 40 or 80 fmol/ml (1 or 2 ng/ml), and still preferably higher than 0.160 pmol/ml (4 ng/ml).

Advantageously, the administrated amount of the at least one conjugate is less than 2.4 nmol/kg (60 mcg/kg), preferably less than 2 nmol/kg (50 mcg/kg) or 1.2 nmol/kg (30 mcg/kg), and still preferably less than 1.0 nmol/kg (25 mcg/kg) or even less than 200 pmol/kg (5 mcg/kg).

Still advantageously, the administrated amount of the at least one conjugate corresponds to a blood concentration of less than 0.12 nmol/ml (3,000 ng/ml), preferably less than 80 or 40 pmol/ml (2,000 or 1,000 ng/ml), and still preferably less than 20 pmol/ml (500 ng/ml) or even less than 12 pmol/ml (300 ng/ml).

The administrated amount also induces a proliferation of CD8 T cells that is higher than the one obtained with HDIL-2.

In a first preferred embodiment, the conjugate is used for treating a subject suffering from a disease associated with a bad prognosis.

As used herein, a disease associated with a bad prognosis is a disease wherein the median prognosis is less than 2 years, preferably less than 1 year and still preferably less than 6 months.

As used herein, a disease associated with a bad prognosis is an advanced (TNM grade IV) or a metastatic cancer.

In said embodiment, the conjugate is administrated in an amount inducing a proliferation of natural killer cells (NK cells) which is at least 20% higher than the one obtained with HDIL-2; preferably at least 25% higher; and still preferably at least 30% higher than the one obtained with HDIL-2.

In said embodiment, the conjugate is administrated in an amount inducing a proliferation of CD8+ T cells, which is at least 20% higher than the one obtained with HDIL-2; preferably at least 25% higher; and still preferably at least 30% higher than the one obtained with HDIL-2.

As an illustration, an effective amount of the at least one conjugate is comprised between 24 and 2,400 pmol/kg (0.6 and 60 mcg/kg), preferably between 28 and 800 pmol/kg (0.7 and 20 mcg/kg) and still preferably between 32 and 400 pmol/kg (0.8 and 10 mcg/kg).

As an another illustration, the conjugate is administrated in an amount corresponding to a blood concentration comprised between 0.4 pmol/ml and 0.12 nmol/ml (10 ng/ml and 3,000 ng/ml), preferably between 0.48 pmol/ml and 40 pmol/ml (12 ng/ml and 1,000 ng/ml), and still preferably between 0.6 and 20 pmol/ml (15 and 500 ng/ml).

In a second preferred embodiment, said conjugate is used for treating a subject having a good prognosis.

As used herein, a disease associated with a good prognosis is a disease wherein the median prognosis is more than 3 years, preferably more than 4 years and still preferably more than 5 years.

As used herein, a disease associated with a good prognosis is a non-metastatic cancer, preferably a TN grade I, II or III cancer, or an infection.

In said embodiment, the conjugate is administered in an amount inducing a proliferation of natural killer cells (NK cells) which is the same or at the maximum 50 or 25% higher than the one obtained with HDIL-2; preferably the same or at the maximum 20% higher; and still preferably the same or at the maximum 10% higher than the one obtained with HDIL-2.

In said embodiment, the conjugate is administered in an amount inducing a proliferation of CD8+ T cells, which is the same or at the maximum 200% higher than the one obtained with HDIL-2; preferably the same or at the maximum 150% higher; and still preferably the same or at the maximum 100% higher than the one obtained with HDIL-2.

As an illustration, an effective amount of the at least one conjugate is comprised between 2 and 200 pmol/kg (50 and 5,000 ng/kg), preferably between 8 and 200 pmol/kg (200 and 5,000 ng/kg) and still preferably between 20 and 80 pmol/kg (500 and 2,000 ng/kg).

As an another illustration, the conjugate is administered in an amount corresponding to a blood concentration comprised between 40 fmol/ml and 12 pmol/ml (1 ng/ml and 300 ng/ml), preferably between 80 fmol/ml and 12 pmol/ml (2 ng/ml and 300 ng/ml), and still preferably between 0.16 and 4 pmol/ml (4 and 100 ng/ml).

Still surprisingly, the inventors established that said IL-15 derivative NK cells induction is obtained with a regulatory T cells induction inferior to the one obtained with HDIL-2.

In a third preferred embodiment, said conjugate is administrated to the subject in an amount inducing a proliferation of Treg cells (FoxP3$^+$CD4$^+$CD25$^{high}$) which is less to the one obtained with HDIL-2.

Advantageously, the conjugate is administered to the subject in an amount inducing a proliferation of Treg cells which is at least 5% less than the one obtained with HDIL-2; preferably at least 10 or 20% less; and still preferably at least 50% less than the one obtained with HDIL-2.

Accordingly, the NK and CD8 cells induction obtained with the IL-15 derivative is much more efficient than the one induced by HDIL-2 because of the smallest regulatory T cells induction.

Preferably, the conjugate is administered to the subject in an amount, whose ratio of the induced percentage of proliferating NK cells on the induced percentage of proliferating Treg cells is at least 25% higher than the one obtained with HDIL-2; preferably at least 50% higher; and still preferably at least 75% higher than the one obtained with HDIL-2.

Preferably, the conjugate is administered to the subject in an amount whose ratio of induced percentage of proliferating CD8 T cells on the induced percentage of proliferating Treg cells which is at least 25% higher than the one obtained with HDIL-2; preferably at least 50% higher; and still preferably at least 75% higher than the one obtained with HDIL-2.

Introduction of the conjugate in these dose ranges can be carried out as a single treatment or over a series of treatments. In effect, while a single dosage provides benefits and can be effectively utilized for disease treatment/management, a preferred treatment course can occur over several stages; most preferably, said administered amount corresponds to a daily administered amount. This amount can be administered once a day for between one and 20 days, such as between one and 10 days, preferably between 2 and 5 days, and most preferably between 2 and 4 days. Now, the administered amount may be under a long-lasting form resulting in a long-term administration with similar daily blood concentration of conjugate.

In another aspect, the present invention relates to a method for determining the therapeutically efficient amount of conjugate to be administrated to a subject suffering from a cancer, from an infection or from an immunodeficient disorder, said method comprising the step of:
i) contacting peripheral blood mononucleated cells (PBMCs) from said subject with increasing amounts of the conjugate defined previously in culture conditions enabling the proliferation of said PBMCs;
ii) contacting other PBMCs from said subject with High Dose of interleukin-2 (HDIL-2) in culture conditions enabling the proliferation of said PBMCs; and
iv) selecting a therapeutically efficient amount of conjugate, said therapeutically efficient amount of conjugate inducing a proliferation of NK cells of said PBMCs which is the same or higher than the one obtained with HDIL-2.

Preferably, said therapeutically efficient amount of conjugate induces a proliferation of CD8 T cells of said PBMCs which is the same or higher than the one obtained with HDIL-2.

Said selected therapeutically efficient amount is adapted for treating a cancer, an infection or an immunodeficient disorder in said subject.

Still preferably, said therapeutically efficient amount is associated to a ratio of the induced percentage of proliferating NK cells and/or of CD8 T cells on the induced percentage of proliferating Treg cells which is at least 25% higher than the one obtained with HDIL-2; preferably at least 50% higher; and still preferably at least 75% higher than the one obtained with HDIL-2.

Now, said therapeutically efficient amount of conjugate induces a proliferation of NK and/or of CD8 T cells, which is at least 50% higher than the one obtained with the culture medium without conjugate (i.e. without HDIL-2 and IL-15 also).

The culture conditions enabling the proliferation of PBMCs in the presence of HDIL-2 are well known from the skilled person and are described in the examples.

Increasing amounts of conjugate correspond to concentration of conjugate comprised between 4 fmol/ml and 120 pmol/ml (0.1 and 3,000 ng/ml), preferably between 40 fmol/ml and 80 pmol/ml (1 and 2,000 ng/ml), and still preferably between 80 fmol/ml and 40 pmol/ml (2 and 1,000 ng/ml).

HD IL-2 is well known from the skilled person and corresponds to the incubation of PBMC with 50 IU/mL (MURPHY, WELNIAK, BACK et al., *J. Immunol.*, vol. 170, p: 2727-33, 2003; ITOH et al., *Cancer Immunol. Immunother.*, vol. 32(2), p: 88-94, 1990; ETTINGHAUSEN & ROSENBERG, Cancer Res., vol. 46(6), p: 2784-92, 1986).

In a first preferred embodiment, said subject is suffering from a disease associated with a bad prognosis.

In said embodiment, the step iii) corresponds to the selection of an amount of conjugate inducing a proliferation of natural killer cells (NK cells), which proliferation is at least 20% higher than the one obtained with HDIL-2; preferably at least 25% higher; and still preferably at least 30% higher than the one obtained with HDIL-2.

Preferably, the step iii) also corresponds to the selection of an amount of conjugate inducing a proliferation of CD8 T cells, which proliferation is at least 20% higher than the one obtained with HDIL-2; preferably at least 25% higher; and still preferably at least 30% higher than the one obtained with HDIL-2.

In a second preferred embodiment, said conjugate is used for treating a subject having a good prognosis.

In said embodiment, the step iii) corresponds to the selection of an amount of conjugate inducing a proliferation of natural killer cells (NK cells) which is the same or at the maximum least 50 or 25% higher than the one obtained with HDIL-2; preferably the same or the maximum 20% higher; and still preferably the same or at the maximum 10% higher than the one obtained with HDIL-2.

Preferably, the step iii) also corresponds to the selection of an amount of conjugate inducing a proliferation of CD8 T cells, which proliferation is the same or at the maximum 200% higher than the one obtained with HDIL-2; preferably the same or at the maximum 150% higher; and still preferably the same or at the maximum 100% higher than the one obtained with HDIL-2.

In a third preferred embodiment, the method of the invention further comprises the step of:
iii) contacting peripheral blood mononucleated cells (PBMCs) from said subject with increasing equimolar amounts of IL-15 as compared to the conjugate in culture conditions enabling the proliferation of said PBMCs.

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

EXAMPLES

→ For determining the RLI efficiency, we first used an in vitro model corresponding to NK and CD8 T cells purified from human Peripheral Blood Mononuclear Cells (PBMCs) from human healthy donors.

1) Human Lymphocytes Proliferation Induction by RLI

Peripheral Blood Mononuclear Cells (PMOLBC) from healthy volunteers were isolated by FICOLL-HYPAQUE Gradient (LYMPHOPREP™; 1.077 g/mL). Donor blood was obtained in accordance with the official ethics agreement.

Briefly, PBMC are labeled with 2.5 µM of CFSE (Carboxy Fluorescein Succinimidyl Ester) for 5 minutes and washed with NaCl. Then, PBMCs are incubated for three to seven days at 37° C. in humidified 95% air and 5% $CO_2$. Cells are collected and stained with anti-CD3, CD4, CD8, CD56 and LIVE/DEAD® Fixable Aqua to select viable cells. Stained cells are acquired immediately on a FACSCanto II flow cytometer (BD BIOSCIENCES) and analyses were performed using FLOWJO software (TREE STAR).

$2\times10^5$ PBMC per well were cultured in 96-well U-bottom plates in 100 µL of complete medium (RPMOLI 1640+10% heat-inactivated fetal bovine serum (FBS)+1% L-Glutamine+1% non-essential amino acids+1% sodium-pyruvate+1% penicillin-streptomycin). Then, 100 µL of 2× medium were added to the culture for a final concentration of 2.5 pg/ml, 25 pg/ml, 250 pg/ml, 2.5 ng/ml or 25 ng/ml of RLI (SEQ ID no 17 or SEQ ID no 18) produced in CHO cells.

As a negative control, PBMCs were incubated with a culture medium.

As a positive control, PBMCs were incubated with 50 IU/mL (3 ng/mL) of human IL-2 (PROLEUKIN, NOVARTIS PHARMA), said amount being equivalent to high dose of IL-2 for human use (MURPHY, WELNIAK, BACK et al., J. Immunol., vol. 170, p: 2727-33, 2003; ITOH et al., Cancer Immunol. Immunother., vol. 32(2), p: 88-94, 1990; ETTINGHAUSEN & ROSENBERG, Cancer Res., vol. 46(6), p: 2784-92, 1986). As a positive control also, we used 2.5 ng/mL of recombinant human IL-15 (CELLGENIX, PRECLINICAL CELLGRO®) corresponding to the same molarity to HDIL-2.

The percentages of proliferating NK cells, CD8+ T cells and CD4+ T cells were determined daily from day 3 to day 7 by CFSE dilution.

Figure 1:
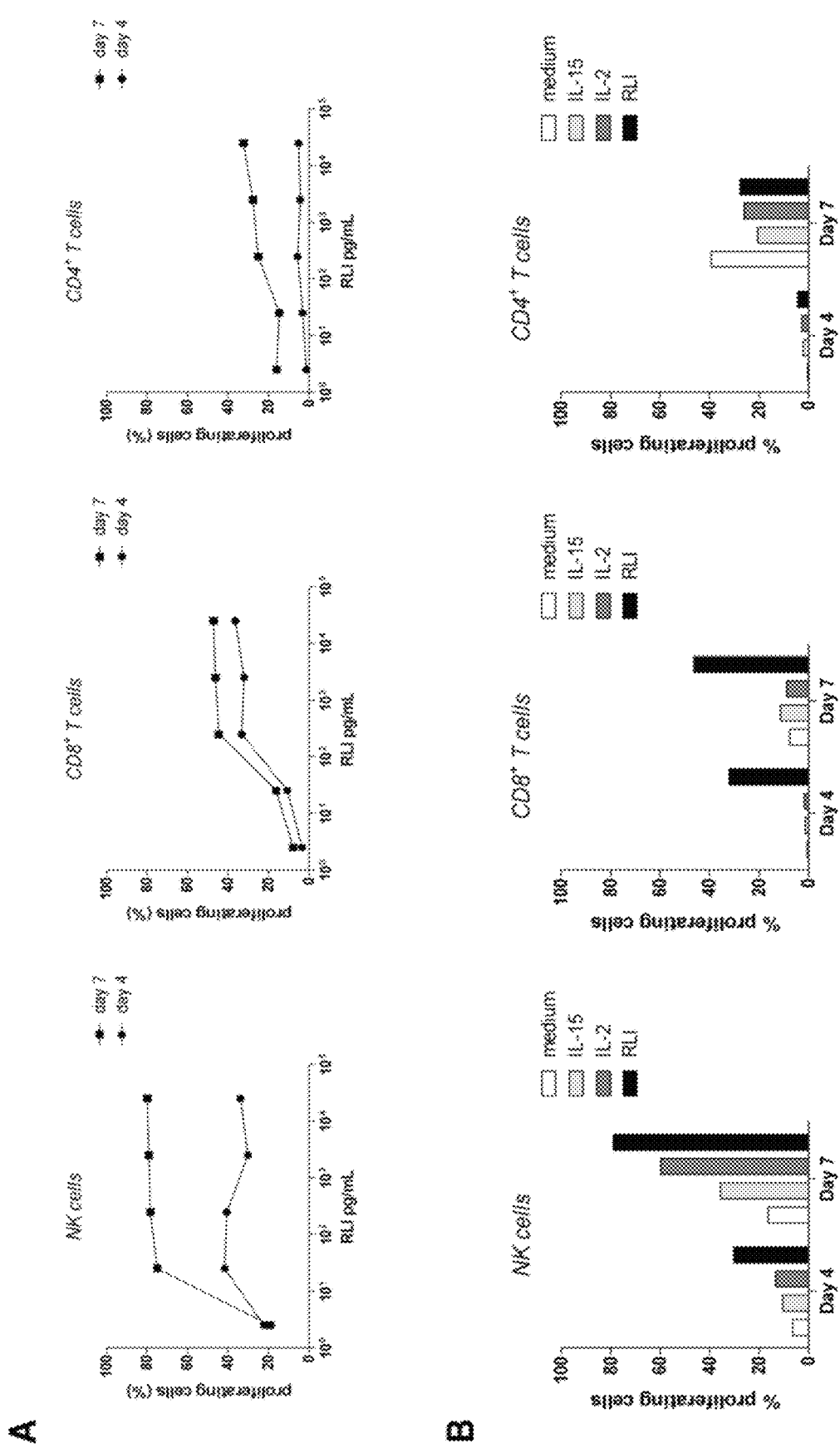
FIG. 1A shows the in vitro dose-effect of RLI on human peripheral blood mononuclear cells (PBMC) for day 4 and day 7.
FIG. 1B shows in vitro dose-effect of RLI on human PBMC as compared to IL-2 and IL-15.

The FIG. 1 shows in vitro dose-effect of RLI on human peripheral blood mononuclear cells (A). Human PBMCs were stained with CFSE on day 0 and then treated for 4 and 7 days with dose-escalating concentrations of RLI (2.5; 25; 250; 2500 and 25000 pg/mL). On day 4 and day 7, PBMCs were harvested, stained and analyzed by Fluorescence-activated cell sorting (FACS). Untreated control cells were simultaneously incubated in medium alone. After exclusion of dead cells and doublets, $CD3^-$ $CD56^+$ are considered as NK cells, $CD3^+$ $CD8^+$ cells are considered as $CD8^+$ T cells and $CD3^+$ $CD4^+$ cells are considered as $CD4^+$ T cells. Proportion of proliferating NK cells (left panel), $CD8^+$ T cells (middle panel) and $CD4^+$ T cells (right panel) are presented in the upper panel A. The FIG. 1B shows the proliferative capacity of RLI, rhIL-15 and rhIL-2 Human PBMCs were treated for 4 and 7 days with RLI at 2.5 ng/mL, rhIL-15 at 2.5 ng/mL and rhIL-2 at 50 UI/mL (3 ng/mL).

The raw data are summarized in Table 1 (NK cells), Table 2 (CD8+ T cells) and Table 3 (CD4+ T cells).

TABLE 1

| | Percentage of proliferating cells among NK cells | | | | | | |
|---|---|---|---|---|---|---|---|
| Day post-incubation | IL-2 50 IU/mL (3000 pg/ml) | IL-15 2500 pg/ml | RLI 2.5 pg/ml | RLI 25 pg/ml | RLI 250 pg/ml | RLI 2500 pg/ml | RLI 25000 pg/ml |
| 3 | 4.71 | 3.69 | 2.04 | 7.66 | 8.43 | 13.7 | 10.4 |
| 4 | 13.40 | 10.50 | 22.20 | 41.70 | 40.50 | 30.2 | 33.8 |
| 5 | 33.70 | 16.40 | 25.80 | 58.40 | 51.10 | 50.2 | 50.6 |
| 6 | 40.40 | 30.70 | 30.30 | 64.30 | ND | 53.7 | 67.5 |
| 7 | 59.80 | 35.60 | 19.30 | 74.90 | 78.20 | 79.0 | 79.8 |

ND: not determined

TABLE 2

Percentage of proliferating cells among CD8+ T cells

| Day post-incubation | IL-2 50 IU/mL (3000 pg/ml) | IL-15 2500 pg/ml | RLI 2.5 pg/ml | RLI 25 pg/ml | RLI 250 pg/ml | RLI 2500 pg/ml | RLI 25000 pg/ml |
|---|---|---|---|---|---|---|---|
| 3 | 0.685 | 2.020 | 0.349 | 1.350 | 3.70 | 9.33 | 9.39 |
| 4 | 1.770 | 1.360 | 3.520 | 10.800 | 33.20 | 32.00 | 36.40 |
| 5 | 5.400 | 3.190 | 2.190 | 11.000 | 39.10 | 51.30 | 46.40 |
| 6 | 9.450 | 4.470 | 2.290 | ND | 28.20 | 45.00 | 46.40 |
| 7 | 8.990 | 11.400 | 7.840 | 16.400 | 44.50 | 46.20 | 47.10 |

ND: not determined

TABLE 3

Percentage of proliferating cells among CD4+ T cells

| Day post-incubation | IL-2 50 IU/mL (3000 pg/ml) | IL-15 2500 pg/ml | RLI 2.5 pg/ml | RLI 25 pg/ml | RLI 250 pg/ml | RLI 2500 pg/ml | RLI 25000 pg/ml |
|---|---|---|---|---|---|---|---|
| 3 | 0.496 | 0.414 | 0.994 | 0.626 | 3.30 | 1.69 | 4.22 |
| 4 | 2.780 | 2.300 | 1.490 | 3.130 | 5.69 | 4.34 | 5.19 |
| 5 | 9.850 | 12.500 | 16.900 | 10.600 | 20.60 | 16.00 | 23.60 |
| 6 | 22.100 | 15.300 | 11.000 | 9.860 | 11.00 | 22.40 | 25.70 |
| 7 | 26.100 | 20.600 | 16.100 | 14.800 | 25.20 | 27.70 | 32.40 |

The results show that, as shown in tables 1 to 3 and FIG. 1, RLI is able to induce some proliferation in vitro with a dose as low as 25 pg/mL (1 fmol/ml) for NK cells and 250 pg/mL for CD8+ T cells.

As shown in table 1 and 2, at doses of 25 and 250 pg/mL, RLI induces equivalent proliferation of NK cells and CD8+ T cells respectively to 2,500 pg/ml rhIL-15 for the first days. Considering the proliferation at day 7, RLI induced NK cells proliferation 300% higher than rhIL-15 at a dose of 250 pg/ml (10 fold less than rhIL-15) and 50% higher at a dose of 25 pg/ml (100 fold less than rhIL-15). At the same day, RLI induced CD8+ cells proliferation 100% higher than rhIL-15 at a dose of 25 pg/ml (100 fold less than rhIL-15). Thus, considering these parameters, RLI is 10 to 100 times more bioactive than rhIL-15.

Conversely, RLI at doses of 250 and 2500 pg/mL showed higher proliferative capacity compared to 3,000 pg/mL IL-2 for NK and CD8+ T cells respectively (Note that equimolar dosage of IL-2 would have been 150 to 1500 pg/mL i.e. 3 to 30 UI/mL) On NK cells, the results show that RLI induced NK cells proliferation 30% higher than rhIL-2 but at a dose of 25 pg/ml (100 fold less than rhIL-2) and equivalent at 2.5 pg/ml (1,000 fold less than rhIL-2). On CD8+ T cells, the efficiency of RLI is nearly 400% higher than hhIL-2 at a dose of 250 pg/ml, 100% higher at a dose of 25 pg/ml and equivalent at a dose of 2.5 pg/ml. Thus, considering these parameters, RLI is at least 2 to 10 times more bioactive than rhIL-2.

The same experiment was reproduced with equimolar concentration of RLI, rhIL-2 and rhIL-15.

Figure 12:
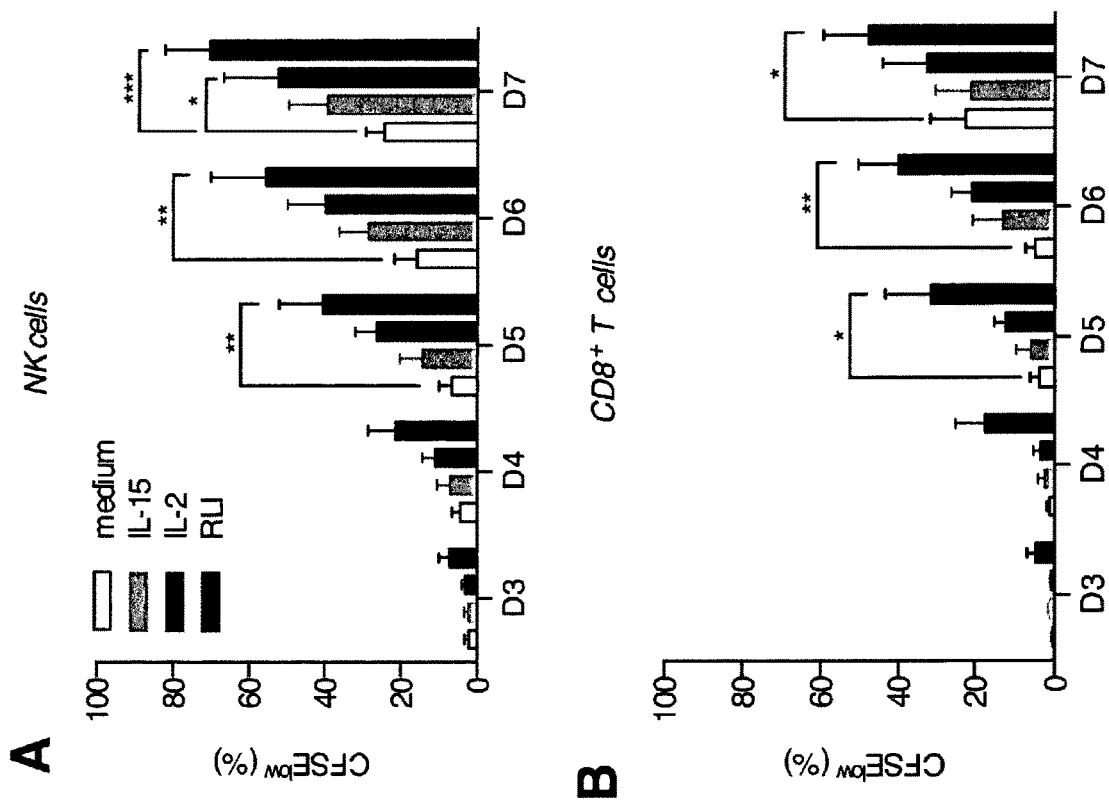
FIG. 12A shows the in vitro proliferation effect at days 3, 4, 5, 6 and 7 on NK cells
FIG. 12B shows the in vitro proliferation effect at days 3, 4, 5, 6 and 7 on CD8⁺ T cells from PBMC of healthy donors of equimolar doses of RLI, IL-2 and IL-15 as compared to PBS.

FIGS. 12A and 12B show the proliferative capacity of RLI, rhIL-15 and rhIL-2 at days 3, 4, 5, 6 and 7 on NK cells and CD8 T cells respectively.

The results confirm that RLI induce a proliferation of NK cells, but also of CD8 T cells, that is greater than the one obtained with equimolar rhIL-15 and also equimolar rhIL-2 and that from the third day following the activation until the seventh day.

2) Human Regulatory T Cells and RLI

Treg cells were analyzed as published elsewhere (MIYARA et al., Immunity, vol. 30(6), p: 899-911, 2009). This strategy allows the discrimination between activated Treg (Foxp3$^{high}$ CD4$^+$ T cells), resting naturally Treg (Foxp3$^{low}$ CD45RA$^+$CD4$^+$ T cells) and activated effector CD4$^+$ T cells (Foxp3$^{Low}$ CD45RA$^-$CD4+ T cells).

Briefly, CFSE-labeled PBMC were obtained as previously described in 1). Two millions of PBMC from healthy volunteers were cultivated in 6-well plates with rhIL-15 (2.5 ng/mL), rhIL-2 (50 IU/mL=3 ng/mL), RLI Pichia (2.5 ng/mL) or medium alone for 6 days. Then cells were harvested and stained with anti-CD3, anti-CD4, anti-CD8 and LIVE/DEAD® Fixable Aqua to select viable cells. Cells were permeabilized following Foxp3 fix/permeabilization protocol (EBIOSCIENCE) and stained with anti-Foxp3. Labelled cells were acquired immediately with a flow cytometer.

Figure 2:
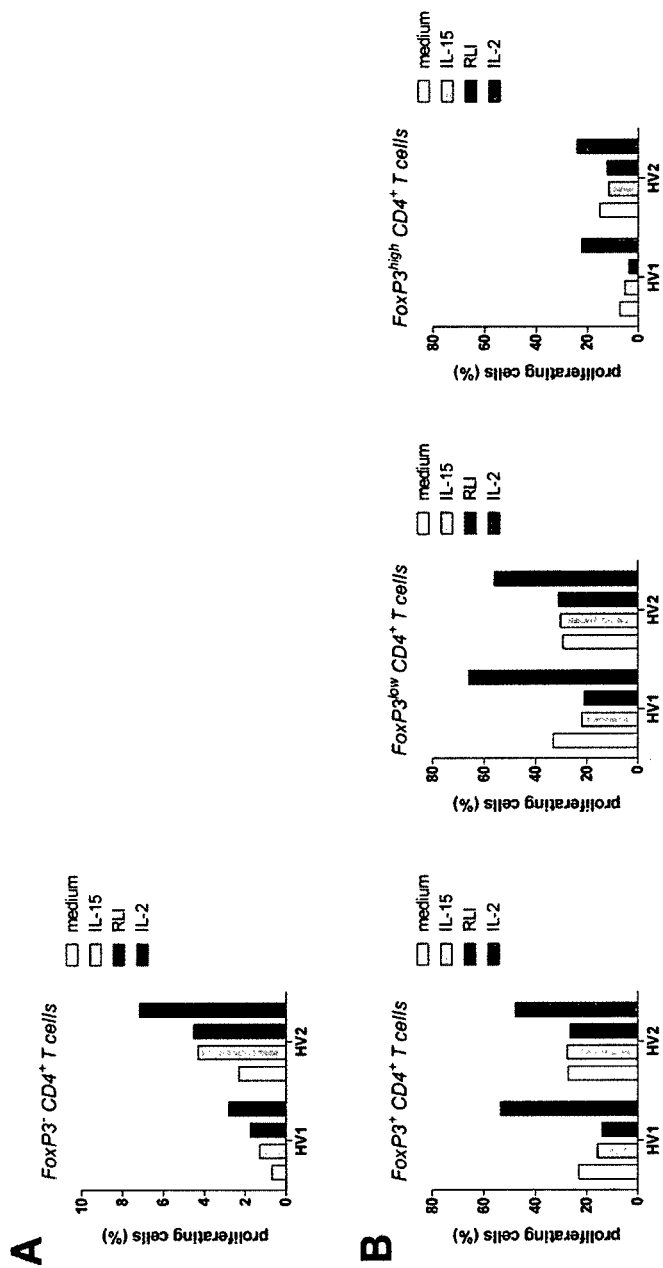
FIG. 2A shows the in vitro effect of RLI on human Treg subpopulation (FoxP3⁻ CD4⁺ T cells) as compared to IL-2 and IL-15.
FIG. 2B shows the proportion of proliferating FoxP3⁺ CD4⁺ T cells (left panel); FoxP3$^{low}$ CD4⁺ T cells (middle panel) and FoxP3$^{high}$ CD4⁺ T cells (right panel) for RLI as compared to IL-2 and IL-15.

The FIG. 2A shows the proportion of proliferating Foxp3$^-$ CD4$^+$ T cells.

The FIG. 2B shows the proportion of proliferating Foxp3$^+$ CD4$^+$ T cells (left panel); Foxp3$^{low}$ CD4$^+$ T cells (middle panel) and Foxp3$^{high}$ CD4$^+$ T cells (right panel).

The results show that RLI does not induce any proliferation of Foxp3$^+$CD4$^+$ T cell subsets. On the other hand, rhIL-2 induces strong proliferation of Foxp3$^+$CD4$^+$ T cell subsets including Foxp3$^{high}$ CD4$^+$ T cells, which are highly suppressive Treg cells.

=> In order to better define the in vivo properties of RLI, we decide to use two complementary animal models corresponding to:

1) first, the macaque which is a good in vivo model for studying drug activity and drug pharmacokinetic; and 2) second, the mouse, which is a good in vivo model for studying cytokine side effects and more particularly vascular leak syndrome (VLS), since macaque can not be used for predicting human VLS.

3) Mouse: RLI Safety Confirmation

Simultaneously, we wanted to determine the RLI safety as compared to similar doses of hIL-2 and of hIL-15. For this purpose, we used mice as an animal model of for immune cells activation and for human VLS. In a first time, we determined RLI activity in this animal model.

a) Bioactivity of RLI in Mouse In Vivo Model

Figure 3:
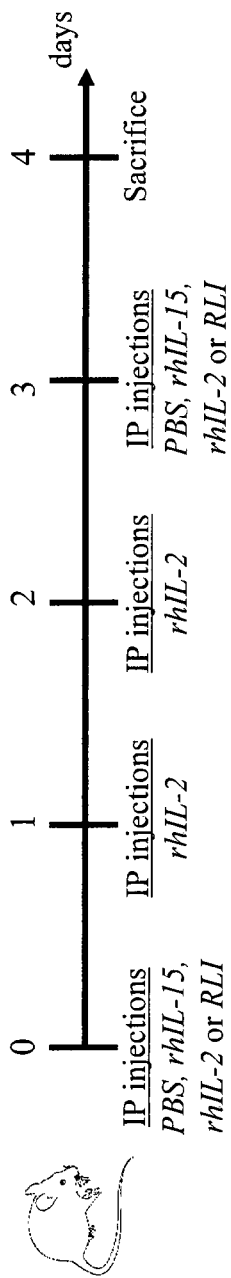
FIG. 3 resumes the protocol of *Mus musculus* injection.

C57BL/6 mice obtained from Harlan Laboratories were injected in intraperitoneal (i.p) with 100 µL of PBS, as a negative control, rhIL-2 (250 000 IU/mouse) as a positive control, rhIL-15 (1.2 µg/mouse) as comparison and RLI (2.5 µg/mouse) following the presented protocol in FIG. 3.

Mice were killed by cervical dislocation and spleens are withdrawn on day 4. Spleen was dissociated in a single-cell suspension on a 100 µm-cell strainer with a back of a syringe. Then, blood cells were lysed using ACK solution (Ammonium-Chloride-Potassium). Splenocytes were washed twice times in a complete medium and viable cells were counted using KOVA slides. Two millions of splenocytes were stained with following antibodies: anti-CD3, anti-CD4, anti-CD8, NKp46 and LIVE/DEAD® Fixable Aqua to select viable cells. Then, splenocytes were permeabilized according to the manufacturing protocol (EBIOSCIENCE FoxP3 permeabilization buffers) and stained with anti-FoxP3 and Ki67. Isotype of Ki67 was used to identify positive cells. Stained cells were acquired immediately on a FACSCANTO II flow cytometer and analyses were performed using FLOWJO SOFTWARE (TREE STAR). NK cells are CD3 negative NKp46 positive cells. CD8+ T cells were analyzed gating on CD3 and CD8 double positive cells. For Regulatory T cells analyses, intra-nuclear staining of Foxp3 was realized to distinguish regulatory from effectors T cells in the CD4 and CD3 double positive population.

Figure 4:
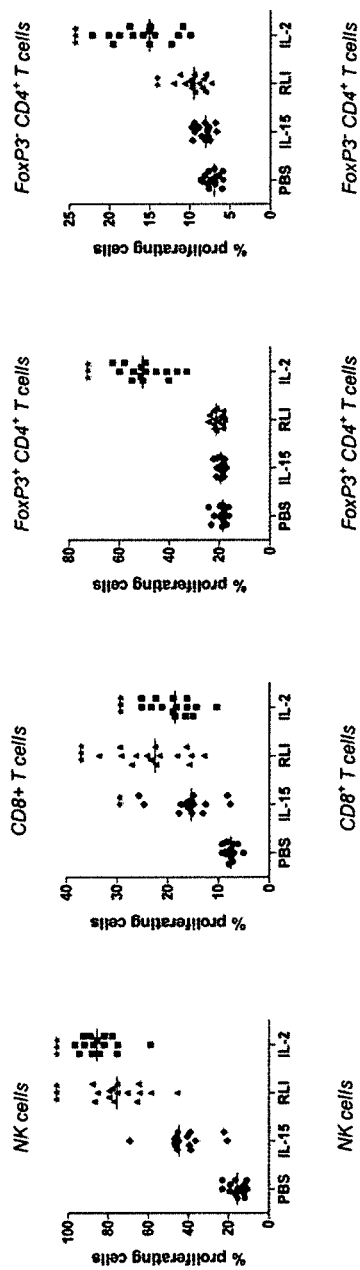
FIG. 4 shows represents the proportion of proliferating NK cells, CD8⁺ T cells, FoxP3⁺ CD4⁺ T cells and FoxP3⁻ CD4⁺ T cells in mice injected with either PBS, IL-2, IL-15 or RLI.

The FIG. 4 represents the proportion of proliferating NK cells, CD8$^+$ T cells, Foxp3$^+$ CD4$^+$ T cells and Foxp3$^-$ CD4$^+$ T cells at day 4.

Figure 5:
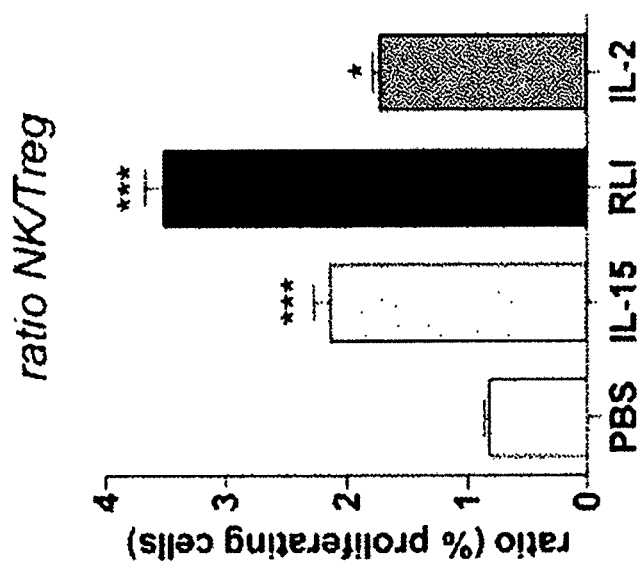
FIG. 5 represents the ratio of proliferating NK cells to FoxP3⁺ T cells (Treg) in mice injected with PBS, IL-2, IL-15 or RLI.

The FIG. 5 shows the ratio of proliferating NK cells to Foxp3$^+$ T cells (Treg) ratio at day 7.

The results show that RLI induces potent proliferation of effector cells without inducing accumulation of Treg as compared to IL-2 and IL-15; these results being the same at days 4 and 7.

Then, we determined immune cells activation in this animal model by RLI as compared to IL-2 and IL-15.

For this, the splenocytes were obtained following previously described protocol.

For secretion assays, splenocytes were cultivated in complete medium supplemented with 5 ng/mL of PMOLA (Phorbol 12-myristate 13-acetate) and 500 ng/mL of Ionomycin during 4 hours. Brefelfin A solution was used to inhibit protein transport (EBIOSCIENCE). Then, cells were collected and stained with following antibodies: anti-CD3, CD4, CD8, NKp46 and LIVE/DEAD® Fixable Aqua to select viable cells. After surface staining, cells were fixed and permeabilized following manufacturing protocol (BD BIOSCIENCES, intracellular staining). Then, permeabilized cells were stained using anti-IFNγ antibody and acquired immediately on a FACS Canto II flow cytometer.

For in vitro cytotoxic assays, NK cells were enriched using mouse NK cell isolation kit II (MILTENYI BIOTECH). Purity was controlled by flow cytometry. $2 \times 10^4$ YAC-1 cells were cultivated in 96-well v-bottom plates with different amounts of NK cells (effector:target ratio (1:1); (5:1) and (10:1)). The final volume was 100 µL per well. After 4 hours of co-culture, supernatants were collected and LDH released was measured using LDH cytotoxicity detection kit (Roche Applied Science). Percentages of cytotoxicity were calculated following this formula: Cytotoxicity (%)=[(("effector: target"–"effector cell control")–"low control")/("high control"–"low control")]×100.

Figure 6:
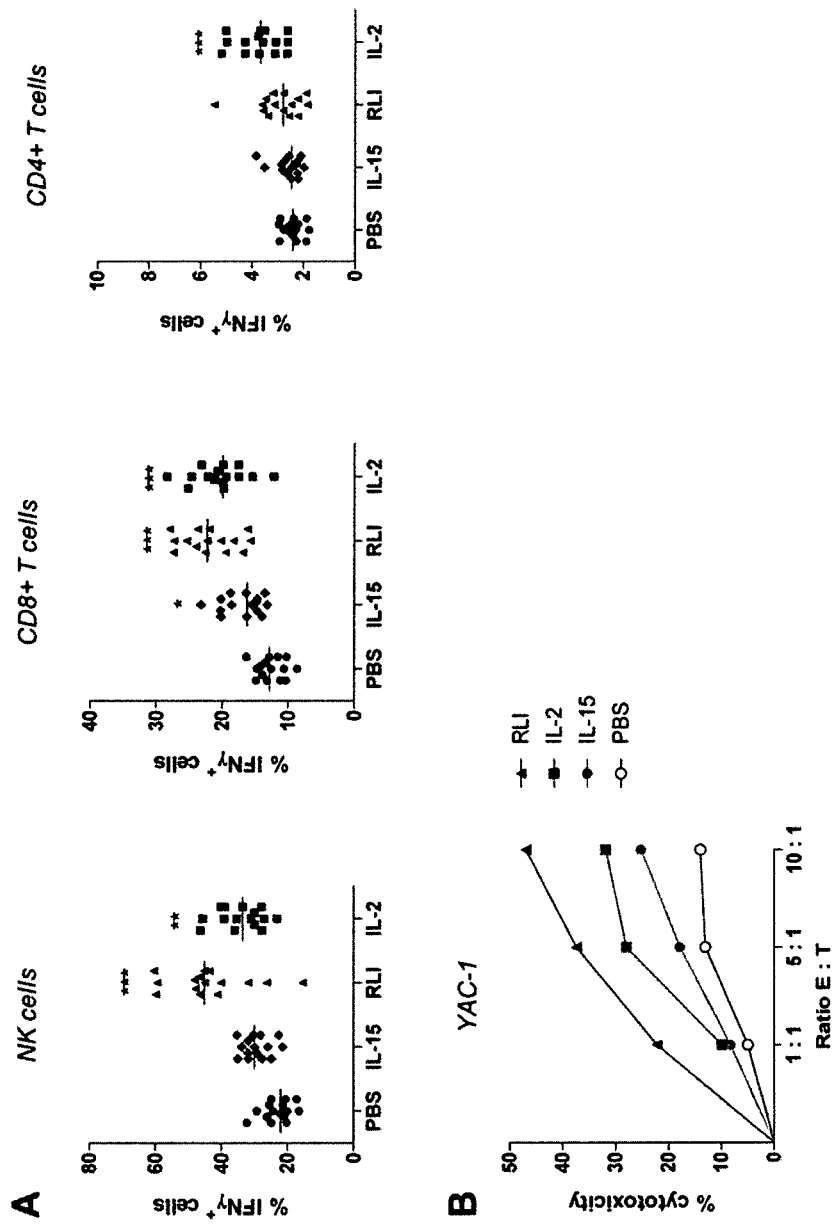
FIG. 6A shows the percentage of IFNγ producing cells among NK cells (left panel), CD8⁺ T cells (middle panel) and CD4⁺ T cells (right panel).
FIG. 6B shows the NK cell cytotoxicity against YAC-1 cell line for the mice injected either with PBS, IL-2, IL-15 or RLI.

The FIG. 6 shows (A) the percentage of IFNγ producing cells among NK cells (left panel), CD8+ T cells (middle panel) and CD4+ T cells were determined (right panel) and (B) the NK cell cytotoxicity against YAC-1 cell line (B) after the mice injected either with PBS, IL-2, IL-15 or RLI.

The results shows that, considering NK cells and CD8+ T cells, RLI showed a stronger bioactivity compared to equimolar dosage of rhIL-15 and to the high dose regimen of IL-2 in vivo in mice (250,000 IU/day i.e. 15 µg/day).

Thus, these data confirm in vitro human data showing that at a dosage as low as 2 µg/injection every 3 days RLI is more bioactive than 15 µg daily injection of IL-2.

So as to better evaluate the safety of RLI, we compared simultaneously in an experimental in vivo tumor model, the anti-tumor activities of such cytokines regimen.

Figure 9A:
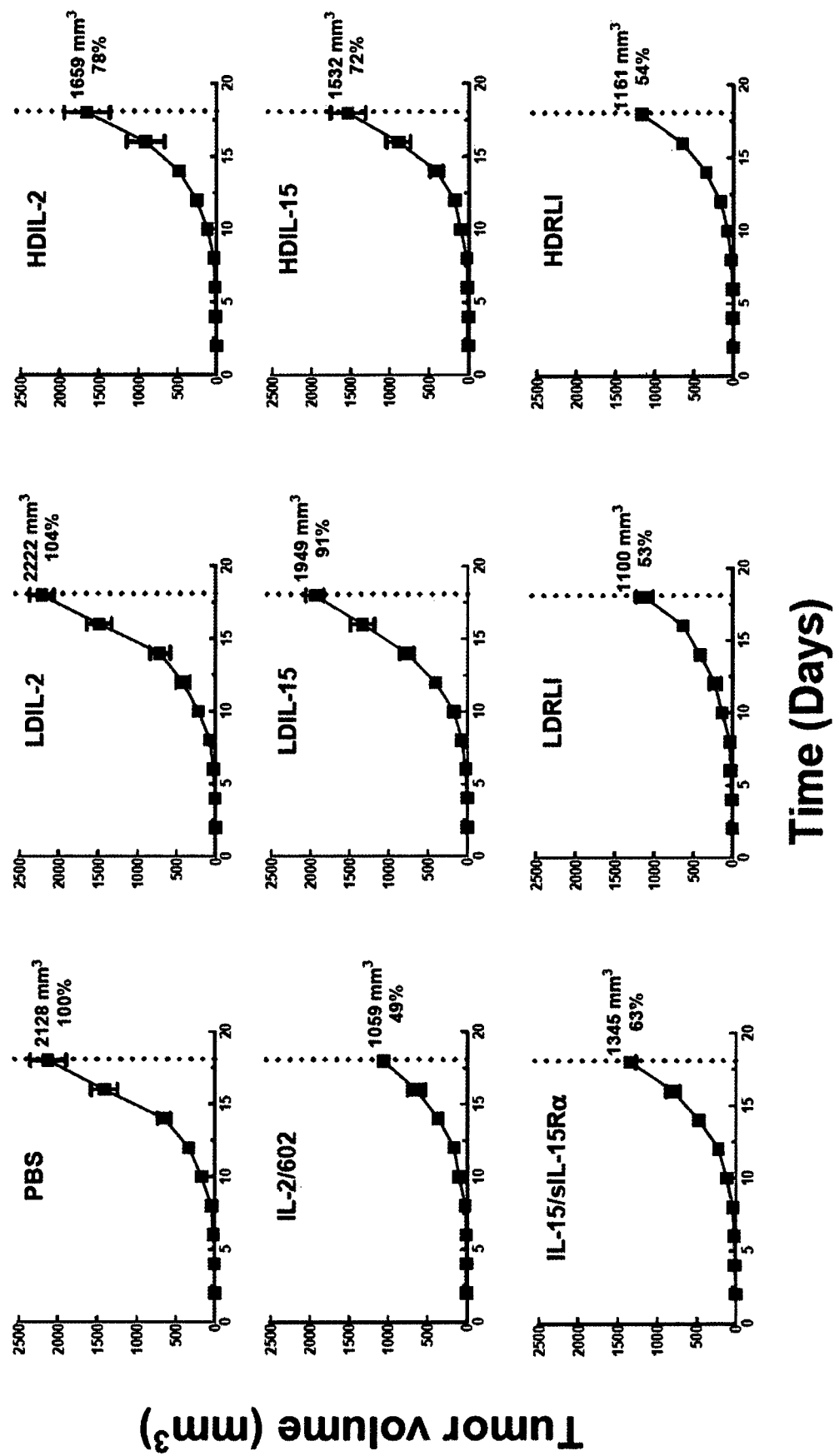
FIG. 9A represents the evolution of the tumor volume depending on the cytokine regimen.
Figure 9B:
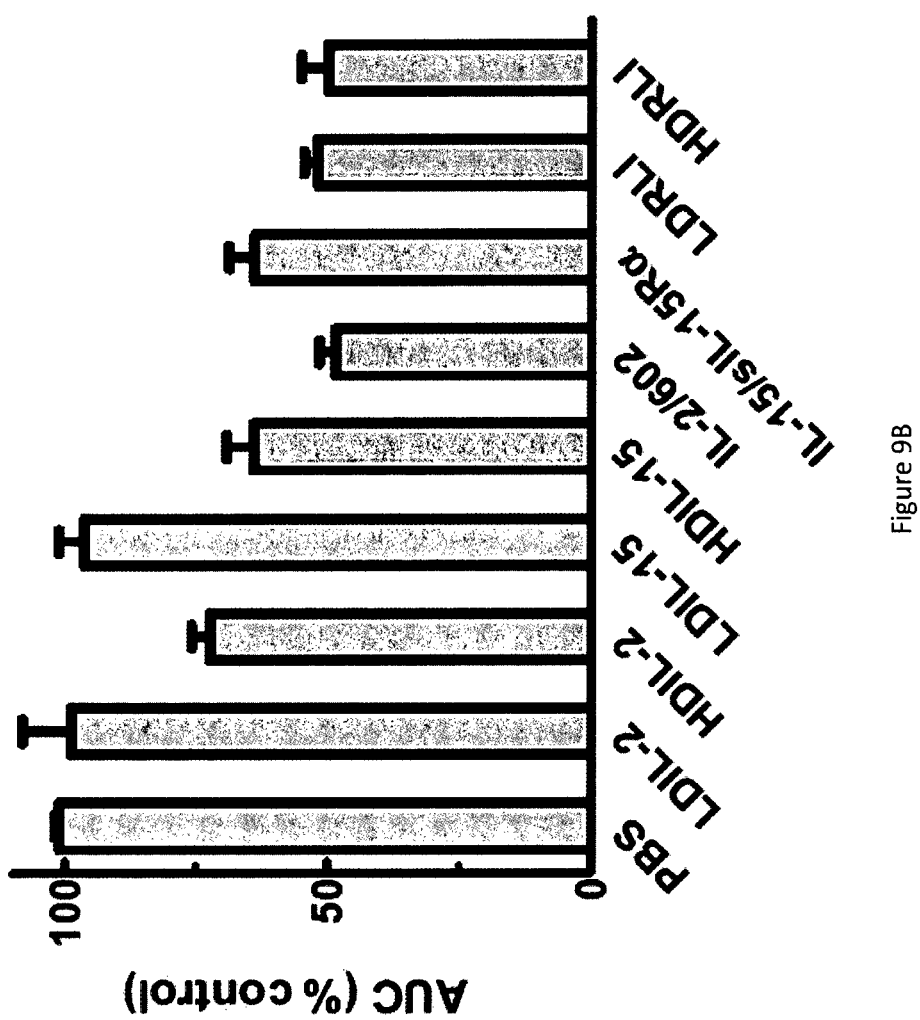
FIG. 9(B) shows the Area Under the Curve (AUC) for subcutaneous tumor growth in mice treated with the indicated reagents.

For this, $10^6$ B16F10 melanoma cells were injected into the upper dermis on the back of mice. Treatment according to the regimen previously described in was started on day 6 after tumor inoculation, at which time-point tumor nodules were clearly visible and palpable at a size of ≈50-55 mm$^3$. Palpable tumors were measured in two perpendicular diameters using calipers, and the radius was estimated by dividing the mean diameter by two. Tumor volume was calculated assuming spherical growth, using the formula $4/3(\pi r3)$ The FIG. 9(A) represents the evolution of the tumor volume depending on the cytokine regimen. The FIG. 9(B) shows the Area Under the Curve (AUC) for subcutaneous tumor growth in mice treated with the indicated reagents. Data are representative of two separate experiments.

As shown in FIGS. 9A and B and in comparison to PBS group, LDRLI decreases primary tumor growth by 47%, which is similar to HDRLI decreasing primary tumor growth by 46%. LDIL-2 has not therapeutic effect, whereas LDIL-15 has a very modest therapeutic effect (-9% on primary tumor growth). Interestingly, HDIL-2 and HDIL-15 present modest but significant therapeutic effects on primary tumor growth (-22% and -28% respectively). IL-15/IL-15Ralpha-Fc decreases the primary tumor growth by 37%, which is less than with LD and HDRLI, despite a similar effect on CD8 T and NK cells. Nevertheless, the ratio CD8/CD4 Treg and NK/CD4 Treg are less favorable with the IL-15/IL-15Ralpha-Fc than with RLI. IL2/602 mAb decreases the primary tumor growth by 51%, which is a little bit higher than with LD or HDRLI, despite a similar effect on CD8 T and NK cells and less favorable ratios CD8/CD4 Treg and NK/CD4 Treg than with RLI. It indicates that the most important immune drivers to control the B6F10 primary tumor growth is more related to the quantitative expansion of CD8 T and NK cells than the relative ratio of these cells with CD4 Treg. Nevertheless, many studies involve the development and activity of CD4 Treg in mouse and human cancers as critical immunosuppressive cells favoring tumor progression through immune escape.

Further in vivo experiments on the metastatic renal cell carcinoma (Renca) confirms the modest but significant therapeutic effects on primary tumor growth of IL-15 and of IL-2, while a strong lung metastasis development inhibition was observed with a ip daily injection at days 1-4 with 2 µg of RLI.

b) Vascular Leak Syndrome (VLS)

Enriched CFSE labeled Ly5.1+CD8+ T cells were transferred to wild-type mice, followed by 4 daily injections of either PBS, 1.5 µg (low dose, LD) or 15 µg (high dose, HD) recombinant human cytokine, including LDIL-2, LDIL-15, HDIL-2 and HDIL-15; 1.5 µg cytokine plus anti-human cytokine antibody (IL-2/602); 1.5 µg IL-15 plus soluble IL-15Rα-Fc (IL-15/sIL-15Rα also called IL-15 non covalent complex); and 2.25 µg RLI (LD RLI) or 15 µg RLI (HD RLI). This IL-2 dose can be considered so as highest limit dose in term of VLS induction, on the basis of safety—i.e. acceptable risk-benefit balance-, said HDIL-2.

On day 5, spleen cells were analyzed for (A) CFSE profiles of donor Ly5.1+CD8+ cells, host CD44high CD122high memory-phenotype CD8+ T cells (MP CD8+), CD4+CD25+ regulatory T cells (Treg) and CD3-NK1.1+ natural killer cells (NK).

Figure 7:
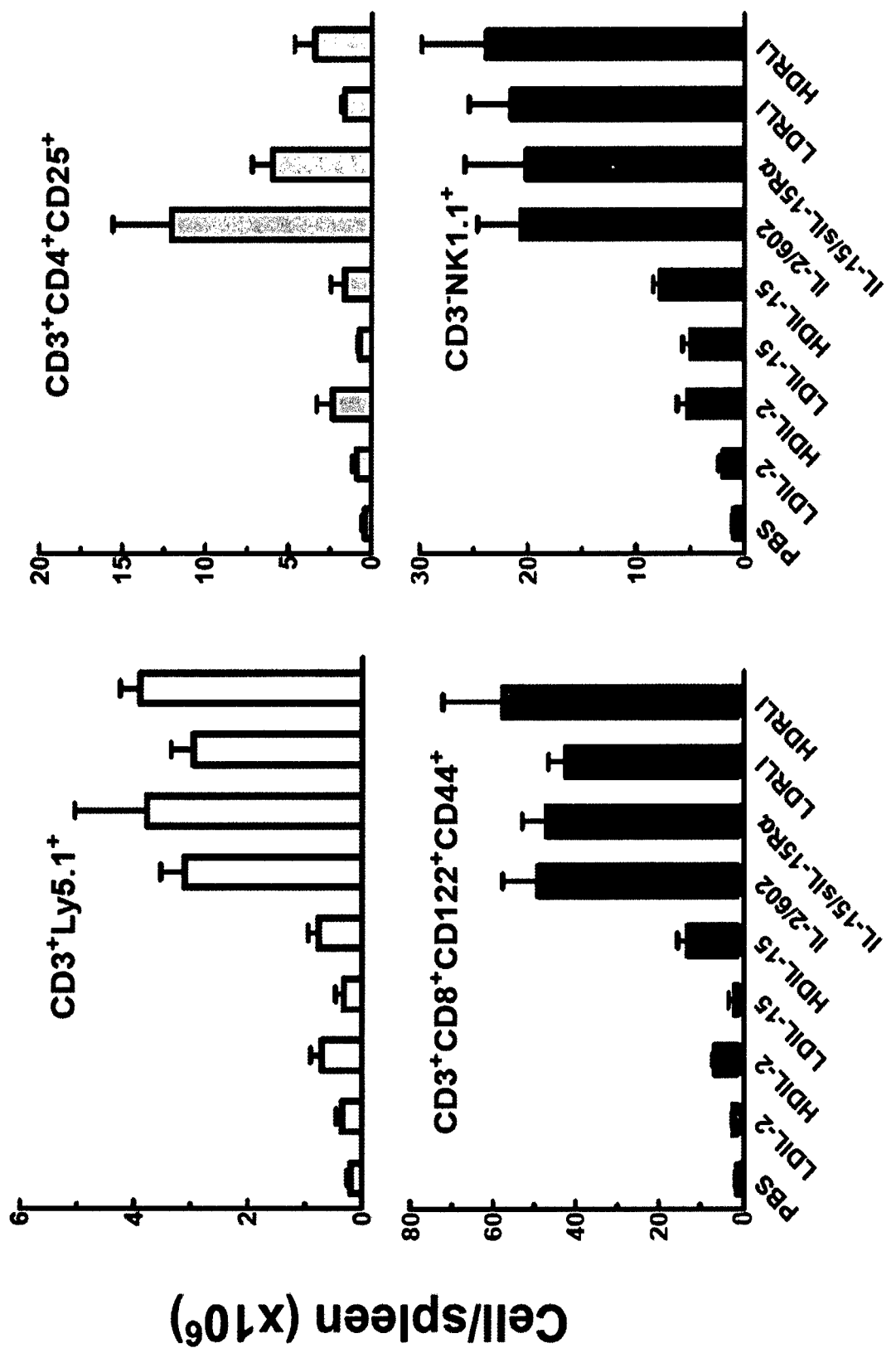
FIG. 7 shows the total cell numbers of donor cells, MP CD8+ T cells, and NK cells in mice injected with donor cells and PBS, IL-2, IL-15 or RLI.

The FIG. 7 shows the total cell numbers of donor cells, MP CD8+ T cells, and NK cells were calculated. Data are representative of two separate experiments.

The results show that LDRLI induces a strong proliferation and expansion of transferred Ly5.1+ CD8+ T cells, enriched for CD122+ CD44+ cells (effector and central memory CD8 T cells), 89% of proliferating cells versus 97% of proliferating cells in the HDRLI group. Thus, LDRLI or HDRLI induces quasi-similar pharmacological effects on target cells, meaning that such very high concentrations of RLI are not required to achieve maximal pharmacological effects.

LDRLI induces much more proliferation of transferred CD8 T cells than equimolar LDIL-2 (12%), LDIL-15 (13.5%), and even HDIL-2 (52%) or HDIL-15 (62%).

Moreover, LDRLI and HDRLI compare very well with superagonist non-covalent complex of IL-2 (IL2/602 mAb; 98%) and of IL-15 (IL-15/IL-15Ralpha-Fc; 98%).

To conclude, RLI is highly efficient to amplify NK and CD8 T cells with the more limited efficacy on the expansion of CD4 Tregs, presenting the best ability among all the tested reagents and regimens to shift the immunomodulatory balance towards immunocytotoxicity without amplify immunosuppression.

For determining the vascular leakage syndrome (VLS), we evaluated the lung edema related to the ratio between the weights of wet and dry tissues. The mice were exsanguinated under anesthesia. Lung were harvested, immediately weighted and were desiccated for 2 days at 50° C. Water influx was obtained by subtracted dry to wet weights of lungs.

Figure 8:
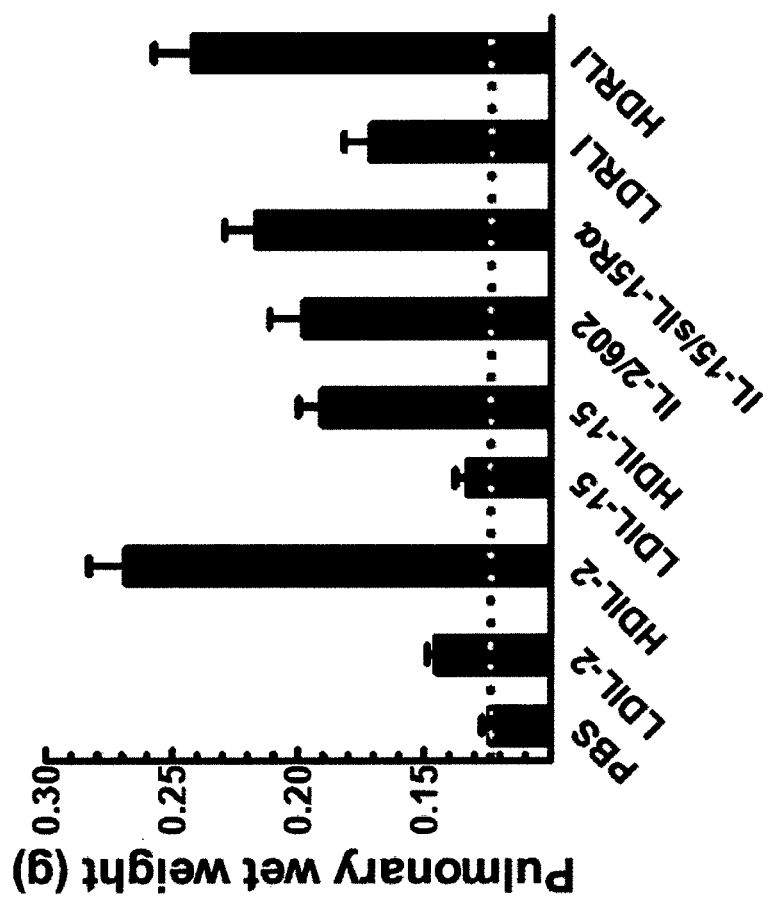
FIG. 8 represents the VLS in mice injected with donor cells and PBS, IL-2, IL-15 or RLI.

The FIG. 8 represents the lung edema (higher than the dotted line) as the percent of the total mice weight. Dotted line represents physiologic background level. Data are representative of two separate experiments.

In comparison to the normal pulmonary wet weight (PWW) from the PBS group, LDIL-15 and LDIL-2 induce a modest increase of PWW of 7.3% and 17.9% respectively. HDIL-15 and HDIL-2 increase the PWW of about 54.5% and 120% respectively. HDIL-2 induces a very important PWW increase, consistent with the vascular leakage syndrome arising in some patients treated with HDIL-2. For HDIL-15, the PWW increase is far less than the one induced by HDIL-2, even if such PWW increase is not insignificant.

Surprisingly, the results show that, as compared to the highest limit for VLS, the ones induced by RLI at low and high doses seem acceptable, whereas the NK and CD8+ cells induction by RLI is higher than the one obtained by hIL-15 and hIL-2 (more than 3 fold).

IL-15/IL-15Ralpha-Fc increases the PWW by 76.4%, which is the double of the VLS induced by LDRLI despite a lower therapeutic efficacy. IL-2/602 mAb increases the PWW by 62.6%, which is 39% more than the VLS induced by LDRLI despite similar therapeutic efficacy. In addition, it is interesting to note that HDRLI increase the PWW by 96.7% versus 38.2% in the LDRLI group despite quasi-similar pharmacological effects on NK and CD8 T cells and quasi-similar therapeutic efficacy. So, even if LDRLI and HDRLI compare very well in terms of activity of NK and CD8 T cells and therapeutic activity, meaning that the efficacy plateau is reached with this LD regimen, increasing RLI dose can induce higher VLS, meaning that this toxic effect is not related to the mechanisms involved in treatment efficacy.

Figure 11:
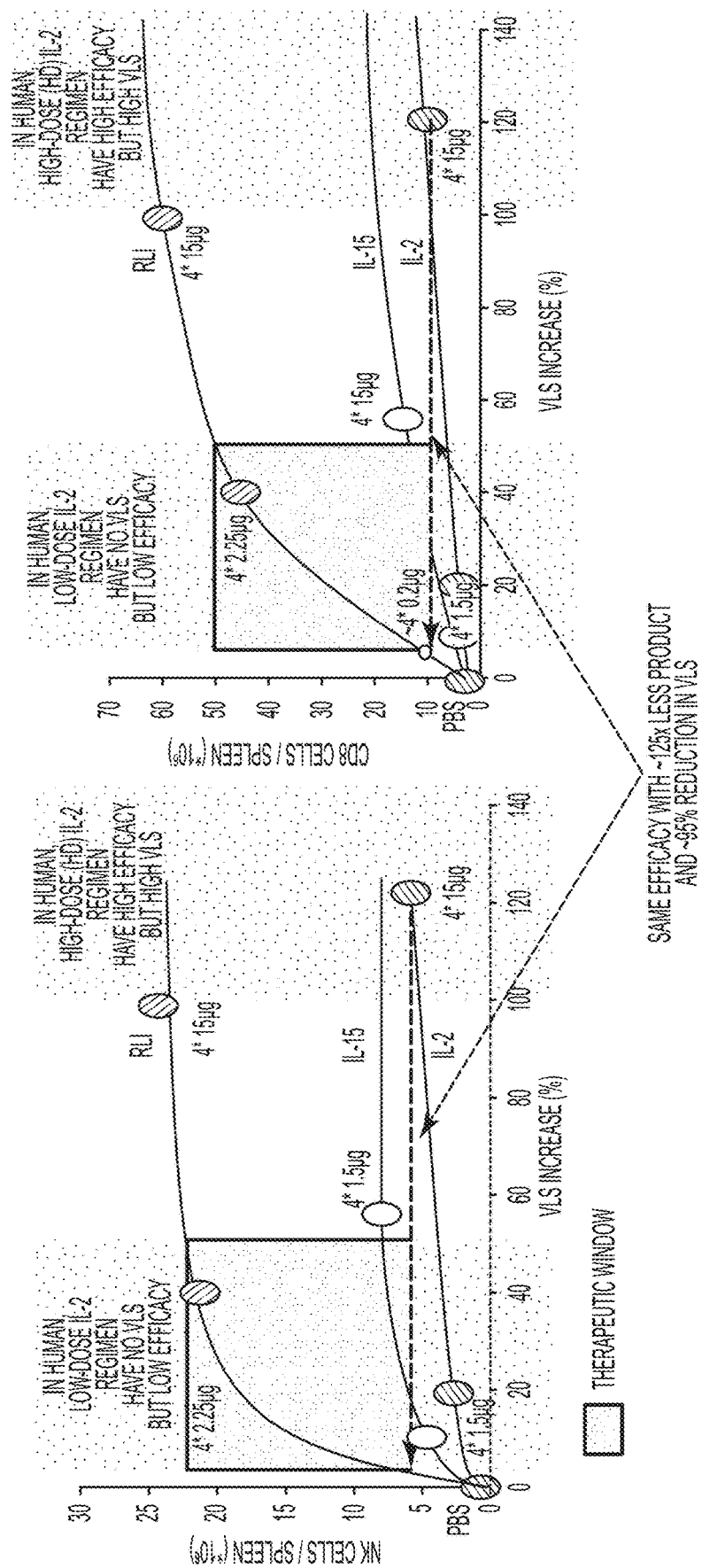
FIG. 11 represents the VLS versus the NK and CD8⁺ cells proliferation induced in mice injected with PBS, IL-2, IL-15, and RLI.

For representing the safety—i.e. strong efficiency and low toxicity—of RLI versus IL-2 and IL-15, the FIG. 11 represent the VLS as a function of NK and CD8+ T cells respectively for the mouse injected with PBS, IL-2, IL-15, and RLI.

Finally, our results show that RLI has a very different safety as compared to the one of IL-2 but also to the one of IL-15 (even if IL-15 and RLI potentially use the same signal pathways), which RLI safety is much more favorable to the one of both IL-15 and IL-2. By consequence, RLI presents improved dose margin and therapeutic window compared to IL-15 and IL-2 to leverage effector immune cells to induce therapeutic effects without side effects. By contrast it appears difficult to achieve a correct stimulation of the immune system with IL-2, and even with IL-15, without inducing rapidly the VLS phenomenon.

c) Dose-Response Effect on NK Cell Expansion Versus Toxicity (VLS)

Dose-ranging effects of RLI on NK cell expansion versus VLS in lung and liver were evaluated according to the protocol as previously described. Mice received 4 daily injections of RLI CHO at 0.2 µg, 0.5 µg, 1 µg, or 2 µg per i.p injection from day 0 to day 3, and then sacrificed at day 4.

The FIG. 13 shows the dose-response effects of RLI on NK cells expansion.

The results show that the RLI treatment induces a dose-dependent expansion of NK cells in spleen with a starting effect from the first dose of 0.2 µg until 2 µg, with a plateau beginning at 1 µg.

In parallel to the NK expansion, VLS was evaluated in lungs and liver of treated mice versus control mice (PBS).

The FIG. 14 shows the dose-response effects of RLI on VLS in lungs and livers in mice.

The results show that the tested doses of RLI do not induce significant VLS in lung and liver in comparison to the PWW of untreated mice. Now, an emerging signal of VLS could be considered as appearing at the highest dose of 2 µg.

Again, dose-ranging effects of RLI on NK cell expansion versus VLS in lung were evaluated according to the protocol as previously described with two new doses. Mice received 4 daily injections of RLI CHO at 0.2 µg, 0.5 µg, 1 µs, 2 µg, 5 µg or 25 µg per ip injection from day 0 to day 3, and then sacrificed at day 4.

The FIG. 15 shows the dose-response effects of RLI on VLS in lungs.

Once again, RLI does not induce VLS in lung from doses 0.2 µg to 2 µg, while RLI at 5 µg and 25 µg induces potent VLS with a similar and maximal intensity.

For NK cells, the FIG. 16 shows the dose response of RLI on NK cell expansion, while the FIG. 17 shows the dose response of RLI on Treg expansion.

Once again, RLI from dose 0.2 to 5 µg per injection induces dose-dependent NK cell expansion in spleen, whereas RLI at 25 µg losses activity and could be considered as detrimental. In parallel, RLI at doses from 0.2 to 2 µg does not increase the percentage of Treg, while these regimens induce similar increase of the number of Treg as compared to the control. In contrast, RLI at highest doses (5 and 25 µg) increase the percentage and the number of CD4 Treg.

The FIG. 18 shows the dose-response effect of RLI on the ration of percentage of CD4 Treg versus NK cells and established that RLI presents a specific dose-dependent activity on NK cell proliferation without specific activity on CD4 Tregs. In addition the margin of doses between 0.2 and 2 μg appears active and safe, reflecting the possibility to stimulate cytotoxic immune cells, like NK cells without inducing VLS. The existence of such a pharmaceutical margin is critical to manage efficacy and safety in patients.

The FIG. 19 recapitulates the comparison between NK and CD8 T cell stimulation versus VLS induced by RLI treatment in healthy mice, in addition to the cell therapeutic effect on Renca cell metastatic development.

Finally, these results confirm the very large safety of RLI, as compared to both IL-15 and IL-2, and established that RLI can be used in a therapeutic window, which is unthinkable for both IL-2 and IL-15: very high dose for bad prognosis patients and very low doses for good prognosis patients.

Pharmacokinetics with the Macaque 4-years old Cynomolgus macaques from about 3 to 4 kgs were injected by RLI (intravenous bolus, 15 min) at different doses (2 macaques at 20 mcg/kg; 2 macaques at 3.5 mcg/kg; macaques).

The study was conducted in compliance with the current GLP regulations as described in the OECD documents "principles of good laboratory practices" (as revised in 1997). This protocol was reviewed by the Ethics Committee of VETAGRO Sup (France) and approved under number 1162. All experiments will be conducted in accordance with the European Directive 86/609/EEC as published in the French Official Journal of Feb. 13, 2001.

Analysis of the pharmacokinetic features was done by performing an ELISA bioassay specific to RLI on the blood serum at different time points: t−72 h as t0, t+10 min, t+30 min, t+1 h, t+4 h, t+6 h, t+24 h and t+72 h. The experimental curve based on measured concentrations was analyzed with a two compartments model with zero under intravenous injection according to the usual equation: fitted concentration=IF(time<tinf;InfR*A*(1−EXP(−_lbd1*time))+InfR*B*(1−EXP(lbdz*time)); InfR*A*(EXP(_lbd1*time))*EXP(−_lbd1*time)+InfR*B*(EXP(lbdz*time))*EXP(−lbdz*time)). (Fitted concentration formula (EXCEL, Fit analysis, two compartment model with zero order intravenous infusion)).

The FIG. 10A represents the observed and modelized evolution of RLI concentration depending on the injected dose as a function of time. Data are representative of two different macaques per dose.

Figure 10:
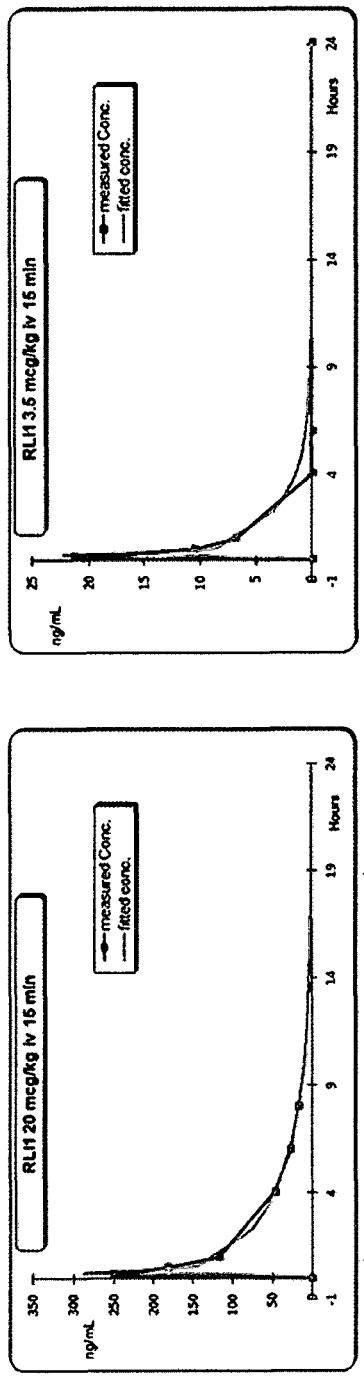
FIG. 10A represents the observed and modelized evolution of RLI concentration in macaque blood depending on the injected dose as a function of time (left panel: 20 mcg/kg RLI1, right panel: 3.5 mcg/kg RLI1).
FIG. 10B represent the remaining concentration of RLI in the whole bloodstream at prolonged time calculated on fitted curves (left panel: 20 mcg/kg RLI1, right panel: 3.5 mcg/kg RLI1).
Figure 10:
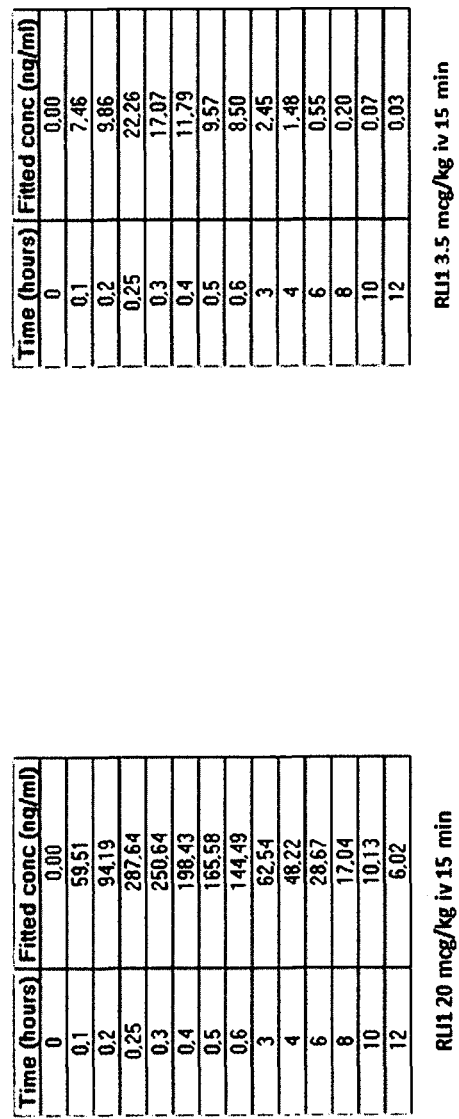

The half-lives of the second compartment ($t^{1/2}\beta$) are about 3 hours for each experiment. Fitted curves permit to evaluate the remaining concentration of RLI in the whole bloodstream at prolonged time, which are represented in FIG. 10 (B).

The results show that for the 20 mcg/kg group, the blood concentrations at 6 h and 12 h are 28.67 and 6.02 ng/ml respectively. For the 3.5 mcg/kg group, the blood concentrations at 6 h and 12 h are 0.55 and 0.03 ng/ml respectively, meaning 550 pg/ml and 30 pg/ml respectively.

According to the tables 1 and 2, such low and very low concentrations are highly efficient to stimulate human NK and CD8 T cells respectively. Now, said NK and CD8 T cells proliferation induction were confirmed in the macaques, while no effect was observed on Treg (data not shown).

For a better conversion of animal doses to Human equivalent dose, theoretical model exist based on BSA.

The determination of human equivalent dose (HED) can be obtained on the basis of the following formula:

HED (mg/kg)=Animal Dose (mg/kg)×(Animal $Km$÷Human $Km$)

In this formula, Km is a correction factor reflecting the relationship between body weight and body surface area.

For a typical adult (body weight 60 lb., body surface area 1.6 m2), Km is 37.

For the most often used laboratory animal species the average Km are 3 for mouse, 6 for rabbit, 12 for macaques, 20 for dog, 37 for human adult (See "Center for Drug Evaluation and Research, Center for Biologics Evaluation and Research. (2002) *Estimating the safe starting dose in clinical trials for therapeutics in adult healthy volunteers*, U.S. Food and Drug Administration, Rockville, Md., USA").

On the basis of said elements, we can approximate some of the maximal human equivalent doses of RLI as compared to the mouse's experiments. Said doses are summarized in table 4.

TABLE 4

| Dose/ injection (mice) mcg | Dose/ injection (20 g) mcg/kg | Dose/ injection (30 g) mcg/kg | Macaque Equivalent dose (20 g) mcg/kg | Macaque Equivalent dose (30 g) mcg/kg | Human Equivalent dose (20 g) mcg/kg | Human Equivalent dose (30 g) mcg/kg |
|---|---|---|---|---|---|---|
| 2.000 | 100.000 | 66.000 | 25.000 | 16.500 | 8.108 | 5.351 |
| 2.250 | 112.500 | 74.250 | 28.125 | 18.563 | 9.122 | 6.020 |
| 15.000 | 750.000 | 495.000 | 187.500 | 123.750 | 60.811 | 40.135 |
| 0.200 | 10.000 | 6.600 | 2.500 | 1.650 | 0.811 | 0.535 |
| 0.020 | 1.000 | 0.660 | 0.250 | 0.165 | 0.081 | 0.054 |

Interestingly, we have shown that high-doses (25 ng/ml) but also very low doses (2.5 pg/ml or 25 pg/ml) can stimulate human NK and CD8 T cells of ex vivo human PBMC (tables 1 and 2, FIG. 1). In macaques, such weak or very weak concentrations can be reached at the peak serum level (0.25 hours) (FIGS. 10A and B). For instance, at a dose of 0.01 mcg/kg in Cynomolgus monkeys, the maximum blood concentration can reach about 62.5 pg/ml according to a quasi-linear regression analysis of experimental curves (FIG. 10B). As shown in table 1, RLI at 25 pg/ml is still superior to HD IL-2 to induce the proliferation on human NK cells. On the basis of these blood concentration in macaque blood and in view of the previous formula, we determined the RLI human equivalent HED RLI) dose for different concentration, which HED RLI are summarized in table 5.

TABLE 5

Illustrations of some minimal human equivalent doses of RLI based on in vivo monkey and ex vivo human PBMC.

| Macaque dose mcg/kg | Maximum blood concentration (macaque) ng/ml | Human Equivalent dose mcg/kg |
|---|---|---|
| Experimental datas | | |
| 20.000 | 287.000 | 6.486 |
| 3.500 | 22.000 | 1.135 |
| 2.500 | 15.625 | 0.811 |
| Extrapolated datas | | |
| 0.500 | 3.125 | 0.162 |
| 0.100 | 0.625 | 0.032 |
| 0.05 | 0.3125 | 0.016 |
| 0.01 | 0.0625 | 0.003 |

By conclusion, the administered daily amount of RLI could vary from 1 ng/kg to 60 mcg/kg, depending of the severity of the disease to be treated.

We claim:

1. A method for inducing proliferation of natural killer cells (NK cells), in a human, comprising:

administering to the human a pharmaceutical composition consisting of a conjugate in an amount sufficient to induce a proliferation of NK cells that is the same or higher than the one obtained with High Dose of interleukin-2 (HDIL-2) and a pharmaceutically acceptable carrier, wherein said conjugate consists of:

a) a polypeptide consisting of the amino acid sequence of interleukin 15 of SEQ ID NO: 3;

b) a polypeptide consisting of the the amino acid sequence of the sushi domain of IL-15Rα selected from the group consisting of SEQ ID NO:8, SEQ ID NO:9 and SEQ ID NO:12; and c) separated by a linker amino acid sequence having a length of 5-30 amino acids, said linker comprising near neutral amino acids selected from the group consisting of Gly (G), Asn (N), Ser (S), Thr (T), Ala (A), Leu (L), and Gln (Q);

wherein the conjugate is a fusion protein; and wherein the amount of conjugate is between 2 to 200 pmol/kg, and wherein the amount of conjugate induces a proliferation of Treg cells that is at least 5% less than the one obtained with HDIL-2.

2. The method of claim 1, wherein said conjugate is administered in an amount that also induces a proliferation of CD8$^+$ T cells higher than the one obtained with HDIL-2.

3. The method of claim 1, wherein said amount of conjugate induces a proliferation of NK cells that is higher than the one obtained with HDIL-2.

4. The method of claim 1, wherein said human has a grade IV cancer according to TNM Classification of Malignant tumors or a metastatic cancer.

5. The method of claim 1, wherein said conjugate is administered in an amount that induces proliferation of NK cells that is at least 20% higher than the one obtained with HDIL-2.

6. The method of claim 1, wherein said conjugate is administered in an amount that induces proliferation of CD8$^+$ T cells that is at least 20% higher than the one obtained with HDIL-2.

7. The method of claim 1, wherein the amount of conjugate induces a proliferation of FoxP3$^+$CD4$^+$CD25$^{high}$ Treg cells that is less than the one obtained with HDIL-2.

8. The method of claim 1, wherein the amount of conjugate results in a ratio of induced proliferating NK cells to induced proliferating Treg cells that is at least 25% higher than the one obtained with HDIL-2.

9. The method of claim 1, wherein the amount of conjugate results in a ratio of induced proliferating CD8$^+$ T cells to proliferating Treg cells that is at least 25% higher than the one obtained with HDIL-2.

10. The method of claim 1, wherein said conjugate consists of the amino acid sequence of the interleukin 15 in a C-terminal position relative to the amino acid sequence of the sushi domain of the IL-15Rα.

11. The method according to claim 1, wherein the amount of conjugate corresponds to a daily administration amount.

12. The method of claim 1, wherein said composition is administered parenterally or intravenously.

13. The method of claim 1, wherein the amount of conjugate is between 8 and 200 pmol/kg.

14. The method of claim 1, wherein the amount of conjugate is between 20 and 80 pmol/kg.

15. The method of claim 1, wherein the amount of conjugate is between 50 and 5,000 ng/kg.

16. The method of claim 1, wherein the amount of conjugate is between 200 and 5,000 ng/kg.

17. The method of claim 1, wherein the amount of conjugate is between 500 and 2,000 ng/kg.

18. The method of claim 1, wherein said conjugate is administered in an amount that induces proliferation of NK cells that is at least 25% higher the one obtained with HDIL-2.

19. The method of claim 1, wherein said conjugate is administered in an amount that induces proliferation of NK cells that is at least 30% higher than the one obtained with HDIL-2.

20. The method of claim 1, wherein said conjugate is administered in an amount that induces proliferation of CD8$^+$ T cells that is at least 25% higher than the one obtained with HDIL-2.

21. The method of claim 1, wherein said conjugate is administered in an amount that induces proliferation of CD8$^+$ T cells that is at least 30% higher than the one obtained with HDIL-2.

22. The method of claim 7, wherein the amount of conjugate induces a proliferation of Treg cells that is at least 10 or 20% less than the one obtained with HDIL-2.

23. The method of claim 7, wherein the amount of conjugate induces a proliferation of Treg cells that is at least 50% less than the one obtained with HDIL-2.

24. The method of claim 1, wherein said linker amino acid sequence is set forth in SEQ ID NO: 13-14.

25. The method of claim 1, wherein the interleukin 15 has the amino acid sequence of SEQ ID NO:3, the sushi domain of IL-15Rα has the amino acid sequence SEQ ID NO:12, and the linker sequence has the amino acid sequence SEQ ID NO:14.

26. The method of claim 1, wherein the linker amino acid sequence length is 15-30 amino acids.

27. The method of claim 1, wherein the linker amino acid sequence length is 15-25 amino acids.

28. The method of claim 1, wherein the linker amino acid sequence length is 18-22 amino acids.

* * * * *